(12) United States Patent
Byers et al.

(10) Patent No.: US 9,889,131 B2
(45) Date of Patent: Feb. 13, 2018

(54) CADHERIN-11 INHIBITORS AND METHODS OF USE THEREOF

(71) Applicant: Georgetown University, Washington, DC (US)

(72) Inventors: Stephen W. Byers, Tacoma Park, MD (US); Sivanesan Dakshanamurthy, Herndon, VA (US); Jaime M. Guidry Auvil, Elkridge, MD (US); Milton L. Brown, Brookeville, MD (US)

(73) Assignee: GEORGETOWN UNIVERSITY, Washington, DC (US)

( * ) Notice: Subject to any disclaimer, the term of this patent is extended or adjusted under 35 U.S.C. 154(b) by 0 days.

(21) Appl. No.: 15/017,040

(22) Filed: Feb. 5, 2016

(65) Prior Publication Data

US 2016/0151363 A1    Jun. 2, 2016

Related U.S. Application Data

(63) Continuation of application No. 14/323,374, filed on Jul. 3, 2014, now Pat. No. 9,284,368, which is a continuation of application No. 13/148,579, filed as application No. PCT/US2010/023556 on Feb. 9, 2010, now Pat. No. 8,802,687.

(60) Provisional application No. 61/151,038, filed on Feb. 9, 2009.

(51) Int. Cl.

| | |
|---|---|
| *A61K 31/498* | (2006.01) |
| *C07D 241/42* | (2006.01) |
| *C07D 213/30* | (2006.01) |
| *A61K 31/343* | (2006.01) |
| *A61K 31/44* | (2006.01) |
| *A61K 31/473* | (2006.01) |
| *A61K 45/06* | (2006.01) |
| *C07D 215/14* | (2006.01) |
| *C07D 307/77* | (2006.01) |
| *C07K 16/18* | (2006.01) |

(52) U.S. Cl.
CPC .......... *A61K 31/498* (2013.01); *A61K 31/343* (2013.01); *A61K 31/44* (2013.01); *A61K 31/473* (2013.01); *A61K 45/06* (2013.01); *C07D 213/30* (2013.01); *C07D 215/14* (2013.01); *C07D 241/42* (2013.01); *C07D 307/77* (2013.01); *C07K 16/18* (2013.01)

(58) Field of Classification Search
CPC .................................................. C07D 241/42
See application file for complete search history.

(56) References Cited

U.S. PATENT DOCUMENTS

| 4,704,692 A | 11/1987 | Ladner |
| 4,816,567 A | 3/1989 | Cabilly et al. |
| 4,845,026 A | 7/1989 | Kung et al. |
| 5,006,459 A | 4/1991 | Kung et al. |
| 7,271,266 B2 | 9/2007 | Finke et al. |
| 2008/0214487 A1 | 9/2008 | Brenner et al. |

FOREIGN PATENT DOCUMENTS

| JP | 2005225978 | 8/2005 |
| WO | 9952365 | 10/1999 |
| WO | 03007959 | 1/2003 |
| WO | 03086394 | 10/2003 |
| WO | 2005076295 | 8/2005 |

OTHER PUBLICATIONS

U.S. Appl. No. 13/148,579, Ex Parte Quayle Action mailed on Jan. 28, 2014, 5 pages.
U.S. Appl. No. 13/148,579, Non-Final Office Action dated Oct. 9, 2013, 9 pages.
U.S. Appl. No. 13/148,579, Notice of Allowance dated Apr. 8, 2014, 9 pages.
U.S. Appl. No. 14/323,374, Final Office Action dated Jul. 23, 2015, 13 pages.
U.S. Appl. No. 14/323,374, Non-Final Office Action dated Apr. 14, 2015, 23 pages.
U.S. Appl. No. 14/323,374, Notice of Allowance dated Nov. 3, 2015, 10 pages.
European Application No. 10739256.5, Extended European search report dated Oct. 25, 2012, 9 pages.
European Application No. 10739256.5, Office Action dated Mar. 6, 2015, 4 pages.
European Application No. 10739256.5, Summons to attend oral proceedings, mailed Jan. 22, 2016, 3 pages.
European Application No. 10739256.5, Communication under Rule 71(3) EPC, Intention to grant, dated Aug. 8, 2016, 7 pages.
Ashburner et al., Gene ontology: tool for the unification of biology. The Gene Ontology Consortium, Nat Genet., vol. 25, Issue 1, 2000, pp. 25-29.
Best et al., Molecular alterations in primary prostate cancer after androgen ablation therapy, Clin Cancer Res., vol. 11, Oct. 1, 2005, pp. 6823-6834.
Bierer et al., Lymphangiogenesis in kidney cancer: expression of VEGF-C, VEGF-D and VEGFR-3 in clear cell and papillary renal cell carcinoma, Oncol Rep., vol. 20, Oct. 2008, pp. 721-725.
Carrasco et al., High resolution genomic profiles define distinct clinico-pathogenetic subgroups of multiple myeloma patients, Cancer Cell, vol. 9, Apr. 2006, pp. 313-325.
Challen et al., Identifying the molecular phenotype of renal progenitor cells, J. Am. Soc. Nephrol., vol. 15, Issue 9, Sep. 2004, pp. 2344-2357.
Christiansen et al., Reassessing epithelial to mesenchymal transition as a prerequisite for carcinoma invasion and metastasis, Cancer Res., vol. 66, Issue 17, Sep. 1, 2006, pp. 8319-8326.
Chu et al., Cadherin-11 promotes the metastasis of prostate cancer cells to bone, Mol Cancer Res., vol. 6, Issue 8, Aug. 2008, pp. 1259-1267.
Ding et al., Parallel synthesis of pteridine derivatives as potent inhibitors for hepatitis C virus NS5B RNA-dependent RNA polymerase, Bioorganic & Medicinal Chemistry Letters, vol. 15, Issue 3, Feb. 1, 2005, pp. 675-678.

(Continued)

*Primary Examiner* — Brian McDowell
(74) *Attorney, Agent, or Firm* — Kilpatrick Townsend & Stockton LLP

(57) ABSTRACT

Cadherin-11 inhibitors and methods for the prevention and treatment of cadherin-11 related diseases are described herein. Cadherin-11 related diseases include cancer and rheumatoid arthritis.

11 Claims, 18 Drawing Sheets

(56) References Cited

OTHER PUBLICATIONS

Edgar et al., Gene Expression Omnibus: NCBI gene expression and hybridization array data repository, Nucleic Acids Res, vol. 30, Issue 1, Jan. 1, 2002, pp. 207-210.

Eisen et al., Cluster analysis and display of genome-wide expression patterns, Proceedings of the National Academy of Sciences, vol. 95, Issue 25, 1998, pp. 14863-14868.

Feltes et al., An alternatively spliced cadherin-11 enhances human breast cancer cell invasion, Cancer Res., vol. 62, Issue 22, Nov. 15, 2002, pp. 6688-6697.

Finak et al., Stromal gene expression predicts clinical outcome in breast cancer, Nat Med., vol. 14, 2008, pp. 518-527.

Gentleman et al., Bioconductor: open software development for computational biology and bioinformatics, Genome Biol., vol. 5, 2004, 16 pages.

Ghosh et al., Estrogenic diazenes: heterocyclic non-steroidal estrogens of unusual structure with selectivity for estrogen receptor subtypes, Bioorganic & Medicinal Chemistry, vol. 11, Issue 4, Feb. 20, 2003, pp. 629-657.

Gupta et al., Adherence of multiple myeloma cells to bone marrow stromal cells upregulates vascular endothelial growth factor secretion: therapeutic applications, Leukemia, vol. 15, Issue 12, 2001, pp. 1950-1961.

Hackam et al., Translation of Research Evidence From Animals to Humans, JAMA, vol. 296, Issue 14, Oct. 11, 2006, pp. 1731-1732.

Handy et al., Disubstituted Pyridines: The Double-Coupling Approach, Journal of Organic Chemistry, vol. 72, Issue 22, 2007, pp. 8496-8500.

Hazan et al., Cadherin switch in tumor progression, Annals of the New York Academy of Sciences, vol. 1014, Apr. 1, 2004, pp. 155-163.

Hu et al., The molecular portraits of breast tumors are conserved across microarray platforms, BMC Genomics, vol. 7, Issue 96, 2006, 12 pages.

Irizarry et al., Exploration, normalization, and summaries of high density oligonucleotide array probe level data, Biostatistics, vol. 4, 2003, pp. 249-264.

Jones et al., Replacing the complementarity-determining regions in a human antibody with those from a mouse, Nature, vol. 321, Issue 6069, 1986, pp. 522-525.

Jordan, Tamoxifen: a most unlikely pioneering medicine, Nature Reviews, Drug Discovery, vol. 2, Mar. 2003, pp. 205-213.

Kang et al., A multigenic program mediating breast cancer metastasis to bone, Cancer Cell., vol. 3, Issue 6, Jun. 2003, pp. 537-549.

Karnoub et al., Mesenchymal stem cells within tumour stroma promote breast cancer metastasis, Nature, vol. 449, Issue 7162, Oct. 4, 2007, pp. 557-563.

Kaupp et al., Quantitative Cascade Condensations between o-Phenylenediamines and 1,2-Dicarbonyl Compounds without Production of Wastes, European Journal of Organic Chemistry, vol. 2002, Issue 8, Apr. 2002, pp. 1368-1373.

Kawaguchi et al., The transition of cadherin expression in osteoblast differentiation from mesenchymal cells: consistent expression of cadherin-11 in osteoblast lineage, J Bone Miner. Res., vol. 16, Issue 2, Feb. 2001, pp. 260-269.

Kiener et al., Cadherin 11 promotes invasive behavior of fibroblast-like synoviocytes, Arthritis and Rheumatism, vol. 60, Issue 5, May 2009, pp. 1305-1310.

Kimura et al., Cadherin-11 expressed in association with mesenchymal morphogenesis in the head, somite, and limb bud of early mouse embryos, Dev Biol., vol. 169, Issue 1, May 1995, pp. 347-458.

Kimura et al., Expression of cadherin-11 delineates boundaries, neuromeres, and nuclei in the developing mouse brain, Dev. Dyn., vol. 206, Aug. 1996, pp. 455-462.

Krishna et al., Expression of cadherin superfamily genes in brain vascular development, J Cereb Blood Flow Metab., vol. 29, Issue 2, Feb. 2009, pp. 224-229.

Lee et al., Androgen Depletion Upregulates Cadherin-11 Expression in Prostate Cancer, The Journal of Pathology, vol. 221, Issue 1, May 2010, pp. 68-76.

Lee et al., Cadherin-11 in Synovial Lining Formation and Pathology in Arthritis, Science, vol. 315, Issue 5814, Feb. 16, 2007, pp. 1006-1010.

Lonberg et al., Human Antibodies from Transgenic Mice, Intern. Rev. Immunol., vol. 13, 1995, pp. 65-93.

Maeda et al., Cadherin switching: essential for behavioral but not morphological changes during an epithelium-tomesenchymal transition, J Cell Sci., vol. 118, Mar. 2005, pp. 873-887.

Monahan et al., A novel function for cadherin 11/osteoblast-cadherin in vascular smooth muscle cells: modulation of cell migration and proliferation, J Vasc Surg., vol. 45, Issue 3, Mar. 2007, pp. 581-589.

Morrison et al., Chimeric human antibody molecules: mouse antigen-binding domains with human constant region domains, Proc Natl Acad Sci U S A., vol. 81, Issue 21, 1984, pp. 6851-6855.

Nakamura et al., Involvement of cell-cell and cell-matrix interactions in bone destruction induced by metastatic MDA-MB-231 human breast cancer cells in nude mice, J Bone Miner Metab., vol. 26, Issue 6, 2008, pp. 642-647.

Neve et al., A collection of breast cancer cell lines for the study of functionally distinct cancer subtypes, Cancer Cell, vol. 10, Issue 6, Dec. 2006, pp. 515-527.

Nutt et al., Gene expression-based classification of malignant gliomas correlates better with survival than histological classification, Cancer Res., vol. 63, Issue 7, Apr. 1, 2003, pp. 1602-1607.

OECD/OCDE, Acute Oral Toxicity—Up-and-Down-Procedure (UDP), OECD Guidelines 425: For the Testing of Chemicals, Oct. 3, 2008, 27 pages.

Orford et al., Serine phosphorylation-regulated ubiquitination and degradation of beta-catenin, The Journal of Biological Chemistry, vol. 272, Issue 40, Oct. 3, 1997, pp. 24735-24738.

Orlandini et al., In fibroblasts Vegf-D expression is induced by cell-cell contact mediated by cadherin-11, J Biol Chem., vol. 276, Issue 9, Mar. 2, 2001, pp. 6576-6581.

Otomasu et al., Synthesis and Conformation of 4,5-disubstituted 5,6-dihydro-4H-imidazo[1,5,4-d,e]quinoxalines, Chemical & Pharmaceutical Bulletin, vol. 21, Issue 3, 1973, pp. 492-496.

Patel et al., Type II cadherin ectodomain structures: implications for classical cadherin specificity, Cell, vol. 124, Issue 6, Mar. 24, 2006, pp. 1255-1268.

International Application No. PCT/US2010/023556, International Preliminary Report on Patentability dated Aug. 18, 2011, 7 pages.

International Application No. PCT/US2010/023556, International Search Report and Written Opinion dated Dec. 30, 2010, 11 pages.

Perou et al., Molecular portraits of human breast tumours, Nature, vol. 406, May 24, 2000, pp. 747-752.

Pishvaian et al., Cadherin-11 is Expressed in Invasive Breast Cancer Cell Lines, Cancer Research, vol. 59, Issue 4, Feb. 15, 1999, pp. 947-952.

Presta, Antibody Engineering, Curr. Op. Struct. Biol., vol. 2, 1992, pp. 593-596.

Przybylo et al., Matrix metalloproteinase-induced epithelial-mesenchymal transition: tumor progression at Snail's pace, Int J Biochem Cell Biol., vol. 39, Issue 6, 2007, pp. 1082-1088.

Rae et al., Evaluation of novel epidermal growth factor receptor tyrosine kinase inhibitors, Breast Cancer Res Treat., vol. 83, Issue 2, Jan. 2004, pp. 99-107.

Rhodes et al., ONCOMINE: a cancer microarray database and integrated data-mining platform, Neoplasia., vol. 6, Issue 1, 2004, pp. 1-6.

Riechmann et al., Reshaping human antibodies for therapy, Nature, vol. 332, Issue 6162, Mar. 1988, pp. 323-327.

Roubinek et al., Substituted 5- and 6-quinoxalinecarboxylic acids and their tuberculostatic activity, Collection of Czechoslovak Chemical Communications, vol. 49, Issue 1, 1984, pp. 285-294.

Saldanha, Java Treeview—extensible visualization of microarray data, Bioinformatics, vol. 20, Issue 17, Nov. 22, 2004, pp. 3246-3248.

(56) References Cited

OTHER PUBLICATIONS

Salon et al., Synthesis, Properties, and Reactions of 5-Substituted Derivatives of 2,3-Diphenylquinoxaline [1], Monatshefte fuer Chemie, vol. 135, Issue 3, 2004, pp. 283-291.

Sarrio et al., Epithelial-mesenchymal transition in breast cancer relates to the basal-like phenotype, Cancer Res., vol. 68, Feb. 15, 2008, pp. 989-997.

Shibata et al., Simultaneous expression of cadherin-11 in signet-ring cell carcinoma and stromal cells of diffuse-type gastric cancer, Cancer Letters, vol. 99, Issue 2, Feb. 6, 1996, pp. 147-153.

Sommers et al., Cell adhesion molecule uvomorulin expression in human breast cancer cell lines: relationship to morphology and invasive capacities, Cell Growth Differ, vol. 2, Aug. 1991, pp. 365-372.

Sorlie et al., Repeated observation of breast tumor subtypes in independent gene expression data sets, PNAS USA, vol. 100, Issue 14, 2003, pp. 8418-8423.

Sun et al., Neuronal and glioma-derived stem cell factor induces angiogenesis within the brain, Cancer Cell, vol. 9, Apr. 2006, pp. 287-300.

Tamura et al., Cadherin-11-mediated interactions with bone marrow stromal/osteoblastic cells support selective colonization of breast cancer cells in bone, Int J Oncol., vol. 33, Jul. 2008, pp. 17-24.

Thiery, Epithelial-mesenchymal transitions in tumour progression, Nat Rev Cancer., vol. 2, Jun. 2002, pp. 442-454.

Tomita et al., Cadherin switching in human prostate cancer progression, Cancer Res., vol. 60, Jul. 1, 2002, pp. 3650-3654.

Valencia et al., Cadherin-11 Provides Specific Cellular Adhesion between Fibroblast-like Synoviocytes, The Journal of Experimental Medicine, vol. 200, Issue 12, Dec. 20, 2004, pp. 1673-1679.

Verhoeyen et al., Reshaping human antibodies: grafting an antilysozyme activity, Science, vol. 239, Issue 4847, Mar. 1988, pp. 1534-1536.

Wang et al., Gene-expression profiles to predict distant metastasis of lymph-node-negative primary breast cancer, The Lancet, vol. 365, Issue 9460, Feb. 19, 2005, pp. 671-679.

Wang et al., Potent, Orally Active Heterocycle-Based Combretastatin A-4 Analogues: Synthesis, Structure-Activity Relationship, Pharmacokinetics, and In Vivo Antitumor Activity Evaluation, Journal of Medicinal Chemistry, vol. 45, Issue 8, 2002, pp. 1697-1711.

Wang et al., Structure-activity relationships for analogues of the phenazine-based dual topoisomerase I/II inhibitor XR11576, Bioorganic & Medicinal Chemistry Letters (Bioorg Med Chem Lett), vol. 12, Issue 3, Mar. 2002, pp. 415-418.

Xekoukoulotakis et al., Synthesis of quinoxalines by cyclization of a-arylimino oximes of a-dicarbonyl compounds, Tetrahedron Letters, vol. 41, Issue 52, 2002, pp. 10299-10302.

Yang et al., A molecular classification of papillary renal cell carcinoma, Cancer Res., vol. 65, Jul. 1, 2005, pp. 5628-5637.

231        231+sd-133
             (100nM)

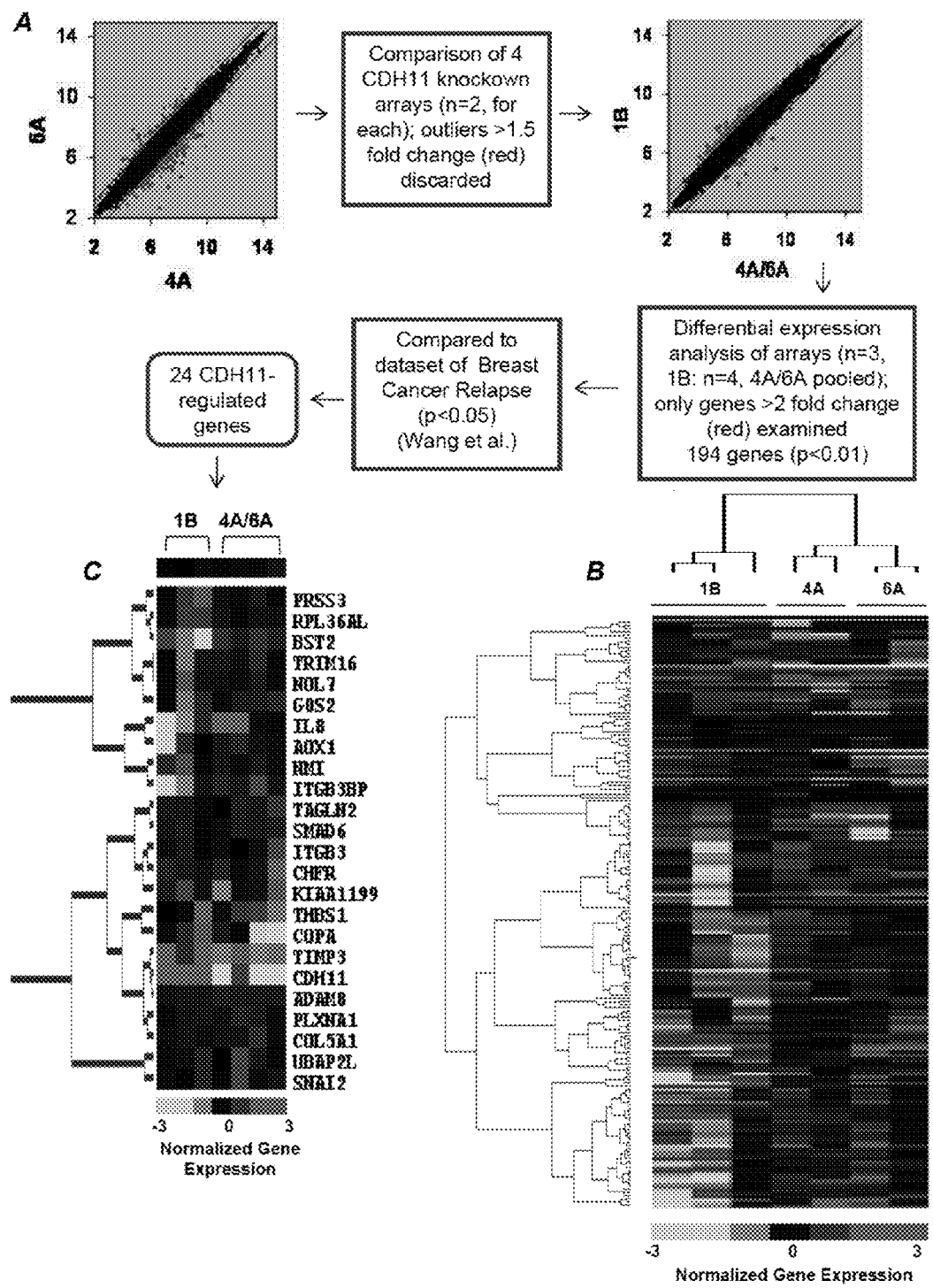
Figs. 14A-C

CADHERIN-11 INHIBITORS AND METHODS OF USE THEREOF

CROSS-REFERENCE TO PRIORITY APPLICATIONS

This application is a continuation of U.S. application Ser. No. 14/323,374, filed Jul. 3, 2014, which is currently pending and which is a continuation of U.S. application Ser. No. 13/148,579, filed Feb. 8, 2012, now issued U.S. Pat. No. 8,802,687, which is a U.S. national stage filing of PCT/US10/23556, filed Feb. 9, 2010, which claims priority to U.S. Provisional Application No. 61/151,038, filed Feb. 9, 2009. These applications are incorporated by reference herein in their entireties.

STATEMENT REGARDING FEDERALLY FUNDED RESEARCH

This invention was made with government support under Grant No. DOD BC062416-01 awarded by the Department of Defense. The government has certain rights in the invention.

BACKGROUND

Advanced epithelial cancers, such as those of the prostate and breast, often exhibit morphologic and molecular changes characteristic of mesenchymal tissue. Breast cancer progression to an invasive metastatic state is hypothesized to represent a form of epithelial-mesenchymal transition (EMT), a process of profound importance during embryogenesis. A process referred to as "cadherin-switching" involves an increased expression of mesenchymal cadherins (often N-cadherin or cadherin-11) in conjunction with down-regulation of epithelial markers (E-cadherin), and is associated with both EMT and tumor progression. Cadherin-11, not normally expressed in normal epithelium, is found in prostate and breast cancer lymph node and bone metastases and its expression directly correlates to disease progression.

SUMMARY

Provided herein are compounds and methods for the prevention and treatment of cadherin-11 related diseases, including cancer and rheumatoid arthritis. A class of compounds for use in the methods described herein includes compounds of the following formula:

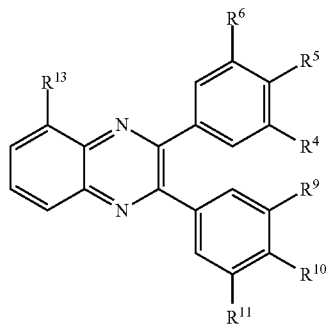

and pharmaceutically acceptable salts and prodrugs thereof. In these compounds, $R^4$, $R^5$, $R^6$, $R^9$, $R^{10}$, and $R^{11}$ are each independently selected from hydrogen, halogen, hydroxyl, substituted or unsubstituted alkoxy, substituted or unsubstituted amido, substituted or unsubstituted amino, substituted or unsubstituted carbonyl, substituted or unsubstituted alkyl, unsubstituted or unsubstituted alkenyl, substituted or unsubstituted alkynyl, unsubstituted heteroalkyl, unsubstituted or unsubstituted heteroalkenyl, substituted or unsubstituted heteroalkynyl, substituted or unsubstituted cycloalkyl, unsubstituted or unsubstituted cycloalkenyl, substituted or unsubstituted cycloalkynyl, substituted or unsubstituted heterocycloalkyl, unsubstituted or unsubstituted heterocycloalkenyl, substituted or unsubstituted heterocycloalkynyl, substituted or unsubstituted aryl, or substituted or unsubstituted heteroaryl; and $R^{13}$ is halogen, hydroxyl, substituted or unsubstituted alkoxy, substituted or unsubstituted amido, substituted or unsubstituted amino, substituted or unsubstituted carbonyl, substituted or unsubstituted alkyl, unsubstituted or unsubstituted alkenyl, substituted or unsubstituted alkynyl, unsubstituted heteroalkyl, unsubstituted or unsubstituted heteroalkenyl, substituted or unsubstituted heteroalkynyl, substituted or unsubstituted cycloalkyl, unsubstituted or unsubstituted cycloalkenyl, substituted or unsubstituted cycloalkynyl, substituted or unsubstituted heterocycloalkyl, unsubstituted or unsubstituted heterocycloalkenyl, substituted or unsubstituted heterocycloalkynyl, substituted or unsubstituted aryl, or substituted or unsubstituted heteroaryl. In some examples, $R^5$ is hydroxyl. In some examples, $R^{10}$ is hydroxyl. In some examples, $R^6$ is chloro. In some examples, $R^{13}$ is hydroxyl, chloro, or carboxyl.

Also described herein are compounds of the following formulas:

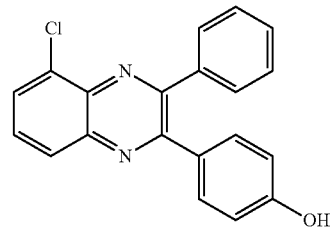

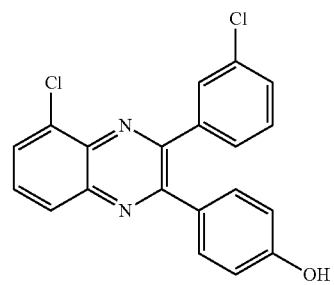

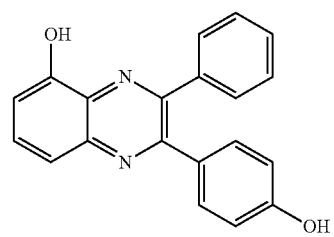

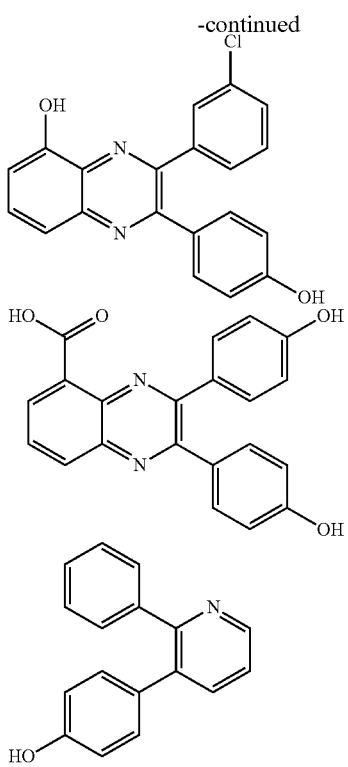

or a pharmaceutically acceptable salt or prodrug thereof.

Also provided herein are compositions including a compound as described above and a pharmaceutically acceptable carrier. Kits, including a compound or composition as described herein, are also provided.

Further provided herein are methods of preventing or treating a cadherin-11 related disease in a subject. Examples of cadherin-11 related diseases include rheumatoid arthritis and cancer (e.g., breast cancer (including basal-like cancer), prostate cancer, glioma, glioblastoma, myeloma, leukemia, poor prognosis/invasive cancer, mesenchymal-like cancer, and metastatic cancer). A method of preventing or treating a cadherin-11 related disease in a subject includes administering to the subject an effective amount of a compound of the following formula:

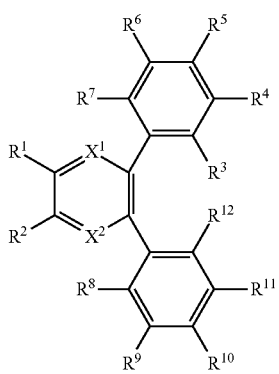

or a pharmaceutically acceptable salt or prodrug thereof. In this method, $R^1$, $R^2$, $R^3$, $R^4$, $R^5$, $R^6$, $R^7$, $R^8$, $R^9$, $R^{10}$, $R^{11}$, and $R^{12}$ are each independently selected from hydrogen, halogen, hydroxyl, substituted or unsubstituted alkoxy, substituted or unsubstituted amido, substituted or unsubstituted amino, substituted or unsubstituted carbonyl, substituted or unsubstituted alkyl, unsubstituted or unsubstituted alkenyl, substituted or unsubstituted alkynyl, unsubstituted heteroalkyl, unsubstituted or unsubstituted heteroalkenyl, substituted or unsubstituted heteroalkynyl, substituted or unsubstituted cycloalkyl, unsubstituted or unsubstituted cycloalkenyl, substituted or unsubstituted cycloalkynyl, substituted or unsubstituted heterocycloalkyl, unsubstituted or unsubstituted heterocycloalkenyl, substituted or unsubstituted heterocycloalkynyl, substituted or unsubstituted aryl, or substituted or unsubstituted heteroaryl; and $X^1$ and $X^2$ are each independently selected from CH or N. In some examples, $R^1$ and $R^2$ are combined to form a substituted or unsubstituted aryl, substituted or unsubstituted heteroaryl, substituted or unsubstituted cycloalkyl, substituted or unsubstituted cycloalkenyl, substituted or unsubstituted cycloalkynyl, substituted or unsubstituted heterocycloalkyl, substituted or unsubstituted heterocycloalkenyl, or substituted or unsubstituted heterocycloalkynyl.

A method of preventing or treating a cadherin-11 related disease in a subject includes administering to the subject an effective amount of a compound of the following formula:

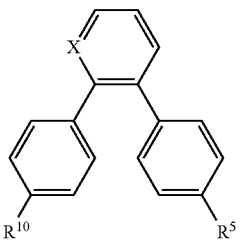

or a pharmaceutically acceptable salt or prodrug thereof. In this method, $R^5$ and $R^{10}$ are each independently selected from hydrogen, halogen, hydroxyl, substituted or unsubstituted alkoxy, substituted or unsubstituted amido, substituted or unsubstituted amino, substituted or unsubstituted carbonyl, substituted or unsubstituted alkyl, unsubstituted or unsubstituted alkenyl, substituted or unsubstituted alkynyl, unsubstituted heteroalkyl, unsubstituted or unsubstituted heteroalkenyl, substituted or unsubstituted heteroalkynyl, substituted or unsubstituted cycloalkyl, unsubstituted or unsubstituted cycloalkenyl, substituted or unsubstituted cycloalkynyl, substituted or unsubstituted heterocycloalkyl, unsubstituted or unsubstituted heterocycloalkenyl, substituted or unsubstituted heterocycloalkynyl, substituted or unsubstituted aryl, or substituted or unsubstituted heteroaryl; and X is selected from CH or N. For example, the compound can be:

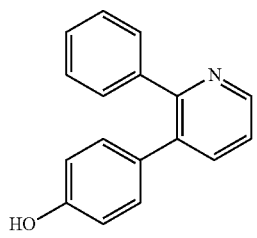 [SMILES: Oc1ccc(-c2cccnc2-c2ccccc2)cc1]

or a pharmaceutically acceptable salt or prodrug thereof.

A method of preventing or treating a cadherin-11 related disease in a subject includes administering to the subject an effective amount of a compound of the following formula:

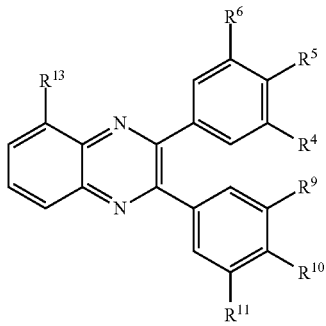

or a pharmaceutically acceptable salt or prodrug thereof. In this method, $R^4$, $R^5$, $R^6$, $R^9$, $R^{10}$, $R^{11}$, and $R^{13}$ are each independently selected from hydrogen, halogen, hydroxyl, substituted or unsubstituted alkoxy, substituted or unsubstituted amido, substituted or unsubstituted amino, substituted or unsubstituted carbonyl, substituted or unsubstituted alkyl, unsubstituted or unsubstituted alkenyl, substituted or unsubstituted alkynyl, unsubstituted heteroalkyl, unsubstituted or unsubstituted heteroalkenyl, substituted or unsubstituted heteroalkynyl, substituted or unsubstituted cycloalkyl, unsubstituted or unsubstituted cycloalkenyl, substituted or unsubstituted cycloalkynyl, substituted or unsubstituted heterocycloalkyl, unsubstituted or unsubstituted heterocycloalkenyl, substituted or unsubstituted heterocycloalkynyl, substituted or unsubstituted aryl, or substituted or unsubstituted heteroaryl. In some examples, $R^5$ is hydroxyl. In some examples, $R^{10}$ is hydroxyl. In some examples, $R^6$ is chloro. In some examples, $R^{13}$ is hydroxyl, chloro, or carboxyl. Further examples of the compounds for use in these methods include:

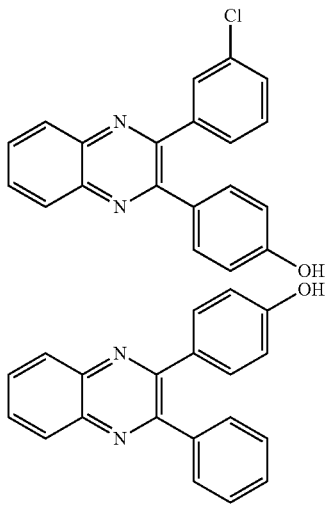

or pharmaceutically acceptable salts or prodrugs thereof.

A method of preventing or treating a cadherin-11 related disease in a subject includes administering to the subject an effective amount of a compound of the following formula:

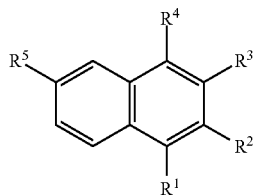

or a pharmaceutically acceptable salt or prodrug thereof. In this method, $R^1$, $R^2$, $R^3$, $R^4$, and $R^5$ are each independently selected from hydrogen, halogen, hydroxyl, substituted or unsubstituted alkoxy, substituted or unsubstituted amido, substituted or unsubstituted amino, substituted or unsubstituted carbonyl, substituted or unsubstituted alkyl, unsubstituted or unsubstituted alkenyl, substituted or unsubstituted alkynyl, unsubstituted heteroalkyl, unsubstituted or unsubstituted heteroalkenyl, substituted or unsubstituted heteroalkynyl, substituted or unsubstituted cycloalkyl, unsubstituted or unsubstituted cycloalkenyl, substituted or unsubstituted cycloalkynyl, substituted or unsubstituted heterocycloalkyl, unsubstituted or unsubstituted heterocycloalkenyl, substituted or unsubstituted heterocycloalkynyl, substituted or unsubstituted aryl, or substituted or unsubstituted heteroaryl. In some examples, one or more of $R^1$ and $R^2$, $R^2$ and $R^3$, or $R^3$ and $R^4$ are combined to form a substituted or unsubstituted aryl, substituted or unsubstituted heteroaryl, substituted or unsubstituted cycloalkyl, substituted or unsubstituted cycloalkenyl, substituted or unsubstituted cycloalkynyl, substituted or unsubstituted heterocycloalkyl, substituted or unsubstituted heterocycloalkenyl, or substituted or unsubstituted heterocycloalkynyl. Examples of compounds for use in these methods include:

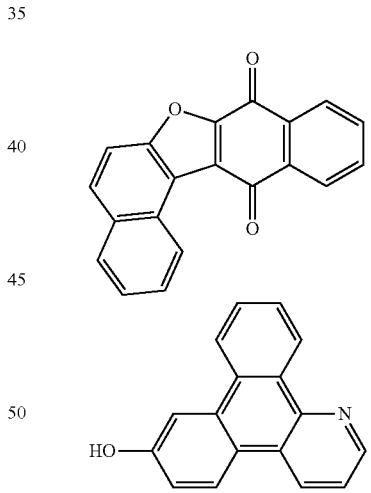

or pharmaceutically acceptable salts or prodrugs thereof.

The methods of preventing or treating a cadherin-11 related disease in a subject as described herein can further include administering a second therapeutic agent to the subject. Examples of second therapeutic agents include chemotherapeutic agents and anti-inflammatory agents.

Further provided are methods of preventing or treating cancer in a subject including selecting a subject with a poor prognosis/invasive cancer and administering to the subject a cadherin-11 inhibitor. Methods of inhibiting tumor growth, invasion, or metastasis in a subject comprising administering to the subject a cadherin-11 inhibitor are also included. The cadherin-11 inhibitor can be, for example, an antibody.

The details of one or more examples of the compounds and methods are set forth in the accompanying drawings and the description below. Other features, objects, and advantages will be apparent from the description and drawings, and from the claims.

DESCRIPTION OF DRAWINGS

FIG. 14A is a flowchart depicting microarray analysis of pooled cell lines [3 controls (1B), 2 each of 4A and 6A knockdown cells] done with a significance of p<0.01 (See Materials and Methods).

FIG. 14B shows a hierarchical cluster analysis between control and knockdown probes resulted in 187 cadherin-11 (CDH11)-regulated genes.

FIG. 14C shows a subset of 24 cadherin-11 (CDH11)-regulated genes associated with clinical outcome in human breast cancer relapse.

DETAILED DESCRIPTION

Figure 1A:
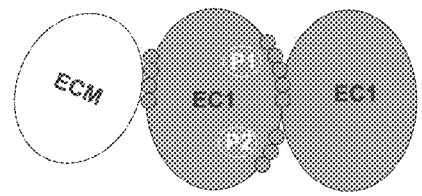
FIG. 1A is a schematic showing the EC1 homodimer of cadherin-11 with P1 and P2 binding pockets.

Epithelial-to-mesenchymal transition (EMT) occurs in malignant transformation and progression. Aggressive cancer cell lines of epithelial origin often appear morphologically similar to mesenchymal cells and generally express various mesenchymal markers. Cadherin-11 expression in breast and prostate cancers represents a form of EMT that the cells utilize to progress and metastasize. Cadherin switching, a phenomenon characterized by down-regulation of the normally-expressed epithelial cadherin concomitant with upregulation of a mesenchymal cadherin, has been observed in various epithelial malignancies, including breast and prostate cancers.

To date, there are few viable treatment options for aggressive, basal-like cancers and/or distant metastasis in breast or prostate cancer. The examples described herein indicate that expression of cadherin-11 in cancer may be indicative of a more aggressive, basal-like cancer that would require specific therapeutics. The cadherin-11 inhibitors described herein block the proliferative and invasive functions of cadherin-11 in aggressive cancer cells. To identify cadherin-11-specific EC1 domain inhibitors, the EC1 domain of cadherin-11 and N-cadherin were compared. Several important differences were revealed, including the fact that cadherin-11 has a larger hydrophobic cleft than N-cadherin, and two Trp residues in cadherin-11, rather than one in N-cadherin, anchor the EC1 homodimer interface. Generally, the cadherin-11 accessible surface area is also larger than that of N-cadherin, indicating that there may be more opportunity for targeting than in the type 1 cadherins. The compounds described herein are readily soluble in DMSO, surpassing the hurdle of hydrophobicity, and are exceptionally potent at nanomolar concentrations, which may indicate solid potential for a targeted therapy that displays inherent low toxicity in patients.

Aggressive breast and prostate cancer cells, MDA-MB-231 and PC-3 cells respectively, preferentially metastasize to the skeleton following intracardiac injection in nude mice. As described in the examples below, depletion of cadherin-11 in PC-3 prostate cancer cells results in a greatly reduced ability to adhere to cadherin-11 in vitro and form skeletal metastases in vivo. As also described in the examples below, primary tumor growth could be prevented upon virtual deletion of cadherin-11 in aggressive MDA-MB-231 breast cancer cells, demonstrating the critical role cadherin-11 plays in tumorigenesis of breast and prostate cancers that express it. The examples described herein show that the reduction of cadherin-11 significantly inhibits proliferation, migration, and invasion of epithelial cancer cells. Further, the examples illustrate that cadherin-11 depletion eliminates tumorigenic potential in vivo. Validation of this result was shown by re-expression of cadherin-11 in the cells, which reverses all observed phenotypes.

Described herein are compounds for use as cadherin-11 inhibitors and methods for the prevention and treatment of cadherin-11 related diseases, including cancer and rheumatoid arthritis. Examples of cancer types include, but are not limited to, renal cell cancer, prostate cancer, breast cancer, glioma, glioblastoma, myeloma, and leukemia. Optionally, the cancer exhibits morphologic and molecular changes characteristic of mesenchymal tissue (i.e., mesenchymal-like cancer) or has a basal-like phenotype (i.e., a basal-like cancer). Optionally, the cancer is metastatic or has a poor prognosis.

The method of preventing or treating a cadherin-11 related disease as described herein includes administering to a subject a cadherin-11 inhibitor. Such inhibitors are administered in an effective amount to prevent or treat one or more symptoms of the cadherin-11 related disease.

A class of cadherin-11 inhibitors includes compounds represented by Formula I:

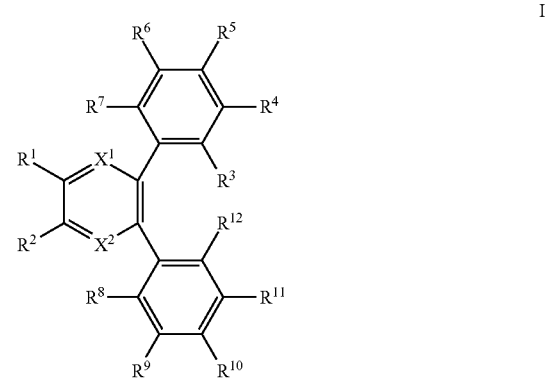

or a pharmaceutically acceptable salt or prodrug thereof.

In Formula I, $R^1$, $R^2$, $R^3$, $R^4$, $R^5$, $R^6$, $R^7$, $R^8$, $R^9$, $R^{10}$, $R^{11}$, and $R^{12}$ are each independently selected from hydrogen, halogen, hydroxyl, substituted or unsubstituted alkoxy, substituted or unsubstituted amido, substituted or unsubstituted amino, substituted or unsubstituted carbonyl, substituted or unsubstituted alkyl, substituted or unsubstituted alkenyl, substituted or unsubstituted alkynyl, unsubstituted heteroalkyl, unsubstituted or unsubstituted heteroalkenyl, substituted or unsubstituted heteroalkynyl, substituted or unsubstituted cycloalkyl, unsubstituted or unsubstituted cycloalkenyl, substituted or unsubstituted cycloalkynyl, substituted or unsubstituted heterocycloalkyl, unsubstituted or unsubstituted heterocycloalkenyl, substituted or unsubstituted heterocycloalkynyl, substituted or unsubstituted aryl, or substituted or unsubstituted heteroaryl.

Also in Formula I, $X^1$ and $X^2$ are each independently selected from CH or N.

In Formula I, $R^1$ and $R^2$ are optionally combined to form a substituted or unsubstituted aryl, substituted or unsubstituted heteroaryl, substituted or unsubstituted cycloalkyl, substituted or unsubstituted cycloalkenyl, substituted or unsubstituted cycloalkynyl, substituted or unsubstituted heterocycloalkyl, substituted or unsubstituted heterocycloalkenyl, or substituted or unsubstituted heterocycloalkynyl.

Examples of Formula I include compounds represented by Formula I-A:

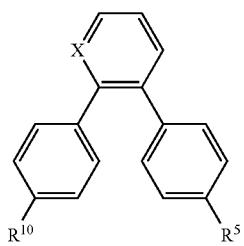

and pharmaceutically acceptable salts and prodrugs thereof.

In Formula I-A, $R^5$ and $R^{10}$ are each independently selected from hydrogen, halogen, hydroxyl, substituted or unsubstituted alkoxy, substituted or unsubstituted amido, substituted or unsubstituted amino, substituted or unsubstituted carbonyl, substituted or unsubstituted alkyl, unsubstituted or unsubstituted alkenyl, substituted or unsubstituted alkynyl, unsubstituted heteroalkyl, unsubstituted or unsubstituted heteroalkenyl, substituted or unsubstituted heteroalkynyl, substituted or unsubstituted cycloalkyl, unsubstituted or unsubstituted cycloalkenyl, substituted or unsubstituted cycloalkynyl, substituted or unsubstituted heterocycloalkyl, unsubstituted or unsubstituted heterocycloalkenyl, substituted or unsubstituted heterocycloalkynyl, substituted or unsubstituted aryl, or substituted or unsubstituted heteroaryl.

Also in Formula I-A, X is selected from CH or N.

An example of Formula I-A includes the following Compound 1.

Compound 1

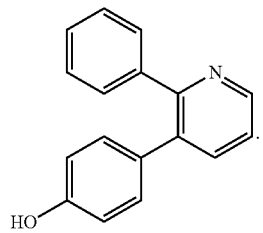

Formula I also includes compounds represented by Formula I-B:

I-B

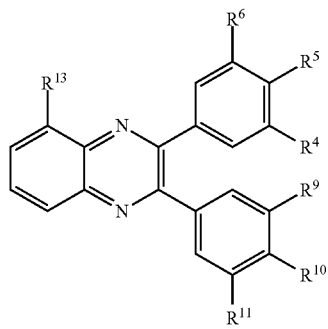

or a pharmaceutically acceptable salt or prodrug thereof.

In Formula I-B, $R^4$, $R^5$, $R^6$, $R^9$, $R^{10}$, $R^{11}$, and $R^{13}$ are each independently selected from hydrogen, halogen, hydroxyl, substituted or unsubstituted alkoxy, substituted or unsubstituted amido, substituted or unsubstituted amino, substituted or unsubstituted carbonyl, substituted or unsubstituted alkyl, unsubstituted or unsubstituted alkenyl, substituted or unsubstituted alkynyl, unsubstituted heteroalkyl, unsubstituted or unsubstituted heteroalkenyl, substituted or unsubstituted heteroalkynyl, substituted or unsubstituted cycloalkyl, unsubstituted or unsubstituted cycloalkenyl, substituted or unsubstituted cycloalkynyl, substituted or unsubstituted heterocycloalkyl, unsubstituted or unsubstituted heterocycloalkenyl, substituted or unsubstituted heterocycloalkynyl, substituted or unsubstituted aryl, or substituted or unsubstituted heteroaryl. In Formula I-B, $R^5$ is optionally hydroxyl. In Formula I-B, $R^6$ is optionally chloro. In Formula I-B, $R^{10}$ is optionally hydroxyl. In Formula I-B, $R^{13}$ is optionally hydroxyl, chloro, or carboxyl. In Formula I-B, $R^{13}$ is optionally not hydroxyl.

Examples of Formula I-B include, but are not limited to, the following compounds:

Compound 2

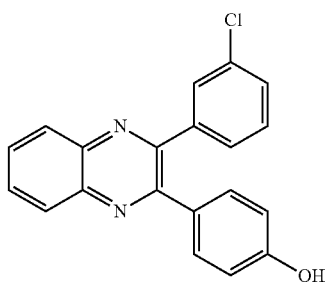

Compound 3

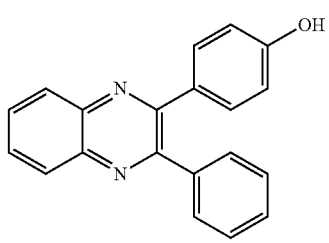

Compound 4

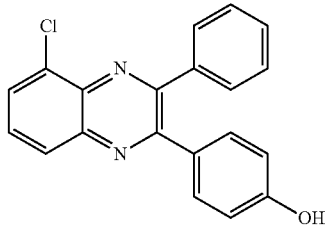 [SMILES: Oc1ccc(-c2nc3cccc(Cl)c3nc2-c2ccccc2)cc1]

Compound 5

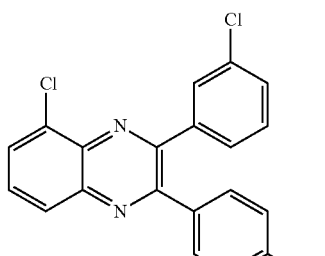

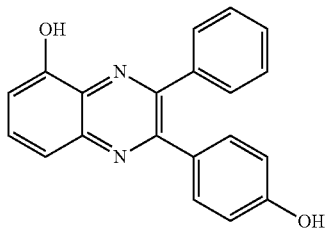

Compound 6

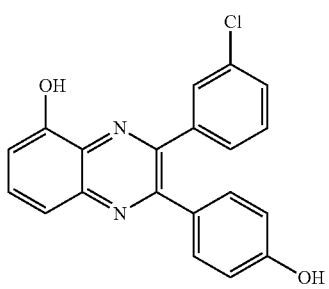

Compound 7

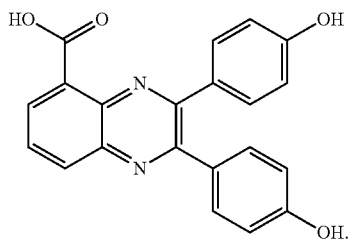

Compound 8

A class of cadherin-11 inhibitors useful in the methods described herein is represented by Formula II:

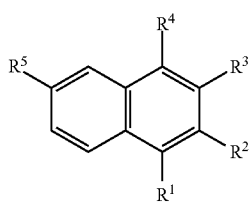

or a pharmaceutically acceptable salt or prodrug thereof.

In Formula II, $R^1$, $R^2$, $R^3$, $R^4$, and $R^5$ are each independently selected from hydrogen, halogen, hydroxyl, substituted or unsubstituted alkoxy, substituted or unsubstituted amido, substituted or unsubstituted amino, substituted or unsubstituted carbonyl, substituted or unsubstituted alkyl, unsubstituted or unsubstituted alkenyl, substituted or unsubstituted alkynyl, unsubstituted heteroalkyl, unsubstituted or unsubstituted heteroalkenyl, substituted or unsubstituted heteroalkynyl, substituted or unsubstituted cycloalkyl, unsubstituted or unsubstituted cycloalkenyl, substituted or unsubstituted cycloalkynyl, substituted or unsubstituted heterocycloalkyl, unsubstituted or unsubstituted heterocycloalkenyl, substituted or unsubstituted heterocycloalkynyl, substituted or unsubstituted aryl, or substituted or unsubstituted heteroaryl.

In Formula II, adjacent R groups on the phenyl ring, i.e., $R^1$, $R^2$, $R^3$, and $R^4$, can be combined to form substituted or unsubstituted aryl, substituted or unsubstituted heteroaryl, substituted or unsubstituted cycloalkyl, substituted or unsubstituted cycloalkenyl, substituted or unsubstituted cycloalkynyl, substituted or unsubstituted heterocycloalkyl, substituted or unsubstituted heterocycloalkenyl, or substituted or unsubstituted heterocycloalkynyl groups. For example, $R^1$ can be a ethylene group and $R^2$ can be an methanimine group that combine to form a $C_6$ heteroaryl. Other adjacent R groups include the combinations of $R^2$ and $R^3$, and $R^3$ and $R^4$.

Examples of Formula II include, but are not limited to:

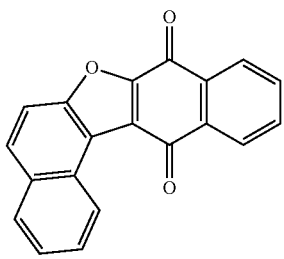

Compound 9

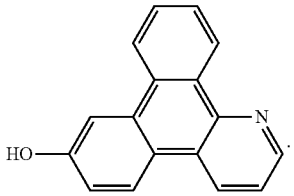

Compound 10

Additional cadherin-11 inhibitors useful in the methods described herein have also been identified that may not be represented by Formula I or Formula II. The structures of these cadherin-11 inhibitors are as follows:

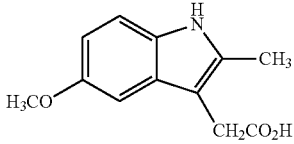

Compound 11

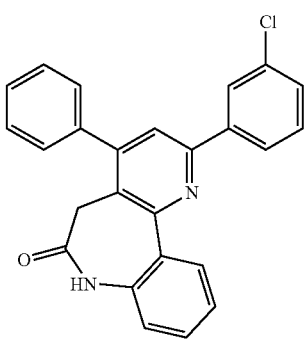

Compound 12

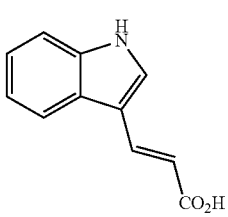

Compound 13

-continued

Compound 14
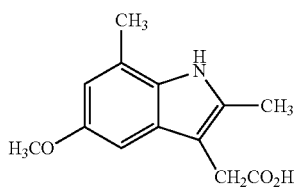

Compound 15
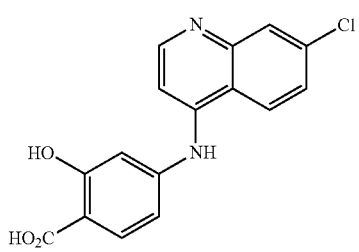

Compound 16
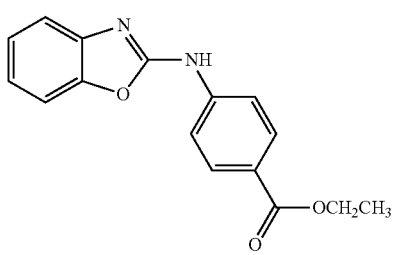

Compound 17
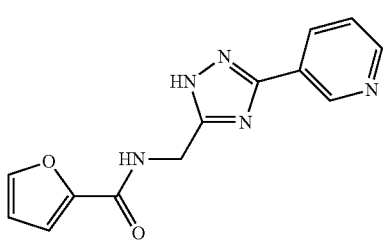

Compound 18
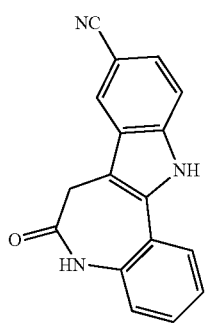

Compound 19
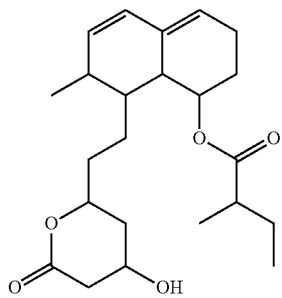

Compound 20
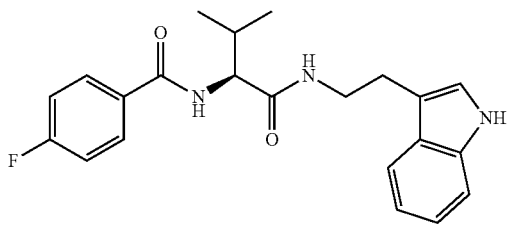

As used herein, the terms alkyl, alkenyl, and alkynyl include straight- and branched-chain monovalent substituents. Examples include methyl, ethyl, isobutyl, 3-butynyl, and the like. Ranges of these groups useful with the compounds and methods described herein include $C_1$-$C_{20}$ alkyl, $C_2$-$C_{20}$ alkenyl, and $C_2$-$C_{20}$ alkynyl. Additional ranges of these groups useful with the compounds and methods described herein include $C_1$-$C_{12}$ alkyl, $C_2$-$C_{12}$ alkenyl, $C_2$-$C_{12}$ alkynyl, $C_1$-$C_6$ alkyl, $C_2$-$C_6$ alkenyl, $C_2$-$C_6$ alkynyl, $C_1$-$C_4$ alkyl, $C_2$-$C_4$ alkenyl, and $C_2$-$C_4$ alkynyl.

Heteroalkyl, heteroalkenyl, and heteroalkynyl are defined similarly as alkyl, alkenyl, and alkynyl, but can contain O, S, or N heteroatoms or combinations thereof within the backbone. Ranges of these groups useful with the compounds and methods described herein include $C_1$-$C_{20}$ heteroalkyl, $C_2$-$C_{20}$ heteroalkenyl, and $C_2$-$C_{20}$ heteroalkynyl. Additional ranges of these groups useful with the compounds and methods described herein include $C_1$-$C_{12}$ heteroalkyl, $C_2$-$C_{12}$ heteroalkenyl, $C_2$-$C_{12}$ heteroalkynyl, $C_1$-$C_6$ heteroalkyl, $C_2$-$C_6$ heteroalkenyl, $C_2$-$C_6$ heteroalkynyl, $C_1$-$C_4$ heteroalkyl, $C_2$-$C_4$ heteroalkenyl, and $C_2$-$C_4$ heteroalkynyl.

The terms cycloalkyl, cycloalkenyl, and cycloalkynyl include cyclic alkyl groups having a single cyclic ring or multiple condensed rings. Examples include cyclohexyl, cyclopentylethyl, and adamantanyl. Ranges of these groups useful with the compounds and methods described herein include $C_3$-$C_{20}$ cycloalkyl, $C_3$-$C_{20}$ cycloalkenyl, and $C_3$-$C_{20}$ cycloalkynyl. Additional ranges of these groups useful with the compounds and methods described herein include $C_5$-$C_{12}$ cycloalkyl, $C_5$-$C_{12}$ cycloalkenyl, $C_5$-$C_{12}$ cycloalkynyl, $C_5$-$C_6$ cycloalkyl, $C_5$-$C_6$ cycloalkenyl, and $C_5$-$C_6$ cycloalkynyl.

The terms heterocycloalkyl, heterocycloalkenyl, and heterocycloalkynyl are defined similarly as cycloalkyl, cycloalkenyl, and cycloalkynyl, but can contain O, S, or N heteroatoms or combinations thereof within the cyclic backbone. Ranges of these groups useful with the compounds and methods described herein include $C_3$-$C_{20}$ heterocycloalkyl, $C_3$-$C_{20}$ heterocycloalkenyl, and $C_3$-$C_{20}$ heterocycloalkynyl. Additional ranges of these groups useful with the compounds and methods described herein include $C_5$-$C_{12}$ heterocycloalkyl, $C_5$-$C_{12}$ heterocycloalkenyl, $C_5$-$C_{12}$ heterocycloalkynyl, $C_5$-$C_6$ heterocycloalkyl, $C_5$-$C_6$ heterocycloalkenyl, and $C_5$-$C_6$ heterocycloalkynyl.

Aryl molecules include, for example, cyclic hydrocarbons that incorporate one or more planar sets of, typically, six carbon atoms that are connected by delocalized electrons numbering the same as if they consisted of alternating single and double covalent bonds. An example of an aryl molecule is benzene. Heteroaryl molecules include substitutions along their main cyclic chain of atoms such as O, N, or S. When heteroatoms are introduced, a set of five atoms, e.g., four carbon and a heteroatom, can create an aromatic system.

Examples of heteroaryl molecules include furan, pyrrole, thiophene, imadazole, oxazole, pyridine, and pyrazine. Aryl and heteroaryl molecules can also include additional fused rings, for example, benzofuran, indole, benzothiophene, naphthalene, anthracene, and quinoline.

The alkyl, alkenyl, alkynyl, aryl, heteroalkyl, heteroalkenyl, heteroalkynyl, heteroaryl, cycloalkyl, cycloalkenyl, cycloalkynyl, heterocycloalkyl, heterocycloalkenyl, or heterocycloalkynyl molecules used herein can be substituted or unsubstituted. As used herein, the term substituted includes the addition of an alkyl, alkenyl, alkynyl, aryl, heteroalkyl, heteroalkenyl, heteroalkynyl, heteroaryl, cycloalkyl, cycloalkenyl, cycloalkynyl, heterocycloalkyl, heterocycloalkenyl, or heterocycloalkynyl group to a position attached to the main chain of the alkyl, alkenyl, alkynyl, aryl, heteroalkyl, heteroalkenyl, heteroalkynyl, heteroaryl, cycloalkyl, cycloalkenyl, cycloalkynyl, heterocycloalkyl, heterocycloalkenyl, or heterocycloalkynyl, e.g., the replacement of a hydrogen by one of these molecules. Examples of substitution groups include, but are not limited to, hydroxyl, halogen (e.g., F, Br, Cl, or I), and carboxyl groups. Conversely, as used herein, the term unsubstituted indicates the alkyl, alkenyl, alkynyl, aryl, heteroalkyl, heteroalkenyl, heteroalkynyl, heteroaryl, cycloalkyl, cycloalkenyl, cycloalkynyl, heterocycloalkyl, heterocycloalkenyl, or heterocycloalkynyl has a full complement of hydrogens, i.e., commensurate with its saturation level, with no substitutions, e.g., linear decane ($-(CH_2)_9-CH_3$).

The compounds described herein can be prepared in a variety of ways. The compounds can be synthesized using various synthetic methods. At least some of these methods are known in the art of synthetic organic chemistry. The compounds described herein can be prepared from readily available starting materials. Optimum reaction conditions can vary with the particular reactants or solvent used, but such conditions can be determined by one skilled in the art by routine optimization procedures.

Variations on Formula I, Formula II, and the additional cadherin-11 inhibitors described above include the addition, subtraction, or movement of the various constituents as described for each compound. Similarly, when one or more chiral centers are present in a molecule, the chirality of the molecule can be changed. Additionally, compound synthesis can involve the protection and deprotection of various chemical groups. The use of protection and deprotection, and the selection of appropriate protecting groups can be determined by one skilled in the art. The chemistry of protecting groups can be found, for example, in Greene, et al., Protective Groups in Organic Synthesis, 2d. Ed., Wiley & Sons, 1991, which is incorporated herein by reference in its entirety.

Reactions to produce the compounds described herein can be carried out in solvents, which can be selected by one of skill in the art of organic synthesis. Solvents can be substantially nonreactive with the starting materials (reactants), the intermediates, or products under the conditions at which the reactions are carried out, i.e., temperature and pressure. Reactions can be carried out in one solvent or a mixture of more than one solvent. Product or intermediate formation can be monitored according to any suitable method known in the art. For example, product formation can be monitored by spectroscopic means, such as nuclear magnetic resonance spectroscopy (e.g., $^1H$ or $^{13}C$) infrared spectroscopy, spectrophotometry (e.g., UV-visible), or mass spectrometry, or by chromatography such as high performance liquid chromatography (HPLC) or thin layer chromatography.

Optionally, in the provided methods the cadherin-11 inhibitor is an antibody. Such antibodies are described, for example, in Valencia et al., J. Exp. Med., 200(12):1673-1679 (2004) and Kiener et al., Arthritis & Rheumatism, 60(5): 1305-1310 (2009), which are incorporated herein by their reference at least for the antibodies and methods of making the antibodies. Such antibodies include, but are not limited to, cadherin-11-2G4, cadherin-11-3H10, and cadherin-11-5H6. These antibodies can be modified as described in more detail below. For example, these antibodies can be modified to produce fragments or chimeric or humanized versions of the antibodies.

Provided is a method of preventing or treating a cadherin-11 related disease in a subject comprising administering to the subject an antibody to cadherin-11. Optionally, as described below the cadherin-11 related disease is cancer. Methods of inhibiting tumor growth, invasion, or metastasis in a subject comprising administering a cadherin-11 inhibitor (e.g., an antibody) is also provided.

As used herein, the term antibody encompasses, but is not limited to, whole immunoglobulin (i.e., an intact antibody) of any class. The term antibody or fragments thereof can also encompass chimeric antibodies and hybrid antibodies, with dual or multiple antigen or epitope specificities, and fragments, such as F(ab')2, Fab', Fab and the like, including hybrid fragments. Thus, fragments of the antibodies that retain the ability to bind their specific antigens are provided. For example, fragments of antibodies that bind cadherin-11 are included within the meaning of the term antibody or fragment thereof. Such antibodies and fragments can be made by techniques known in the art and can be screened for specificity and activity according to the methods set forth in the Examples and in general methods for producing antibodies and screening antibodies for specificity and activity (See Harlow and Lane. Antibodies, A Laboratory Manual. Cold Spring Harbor Publications, New York, (1988)).

Also included within the meaning of antibody or fragments thereof are conjugates of antibody fragments and antigen binding proteins (single chain antibodies) as described, for example, in U.S. Pat. No. 4,704,692, the contents of which are hereby incorporated by reference in their entirety.

Optionally, the antibody is a monoclonal antibody. The term monoclonal antibody as used herein refers to an antibody obtained from a substantially homogeneous population of antibodies, i.e., the individual antibodies comprising the population are identical except for possible naturally occurring mutations that may be present in minor amounts. The monoclonal antibodies herein specifically include chimeric antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired activity (See, U.S. Pat. No. 4,816,567 and Morrison et al., PNAS, 81:6851-6855 (1984)).

Monoclonal antibodies may be prepared using hybridoma methods, such as those described by Kohler and Milstein, Nature, 256:495 (1975) or Harlow and Lane, Antibodies, A Laboratory Manual. Cold Spring Harbor Publications, New York, (1988). In a hybridoma method, a mouse or other appropriate host animal, is typically immunized with an immunizing agent to elicit lymphocytes that produce or are capable of producing antibodies that will specifically bind to the immunizing agent. Alternatively, the lymphocytes may be immunized in vitro. The immunizing agent can be a cadherin-11 or a fragment thereof.

The monoclonal antibodies may also be made by recombinant DNA methods, such as those described in U.S. Pat. No. 4,816,567. DNA encoding the monoclonal antibodies can be readily isolated and sequenced using conventional procedures (e.g., by using oligonucleotide probes that are capable of binding specifically to genes encoding the heavy and light chains of murine antibodies). The hybridoma cells can serve as a preferred source of such DNA. Once isolated, the DNA may be placed into expression vectors, which are then transfected into host cells such as simian COS cells, Chinese hamster ovary (CHO) cells, plasmacytoma cells, or myeloma cells that do not otherwise produce immunoglobulin protein, to obtain the synthesis of monoclonal antibodies in the recombinant host cells. The DNA also may be modified, for example, by substituting the coding sequence for human heavy and light chain constant domains in place of the homologous murine sequences (U.S. Pat. No. 4,816,567) or by covalently joining to the immunoglobulin coding sequence all or part of the coding sequence for a non-immunoglobulin polypeptide. Such a non-immunoglobulin polypeptide can be substituted for the constant domains of an antibody provided herein, or can be substituted for the variable domains of one antigen-combining site of an antibody to create a chimeric bivalent antibody comprising one antigen-combining site having specificity for cadherin-11 and another antigen-combining site having specificity for a different antigen (e.g., a different cancer antigen).

Further provided herein is a humanized or human version of the antibody. Optionally, the antibody activates or inhibits cadherin-11. Optionally, the humanized or human antibody can comprise at least one residue of the framework region of the monoclonal antibody. Humanized and human antibodies can be made using methods known to a skilled artesian; for example, the human antibody can be produced using a germ-line mutant animal or by a phage display library.

Antibodies can also be generated in other species and humanized for administration to humans. Alternatively, fully human antibodies can also be made by immunizing a mouse or other species capable of making a fully human antibody (e.g., mice genetically modified to produce human antibodies) and screening clones that bind cadherin-11. See, e.g., Lonberg and Huszar (1995) Human antibodies from transgenic mice, Int. Rev. Immunol. 13:65-93, which is incorporated herein by reference in its entirety for methods of producing fully human antibodies. As used herein, the term humanized and human in relation to antibodies, relate to any antibody which is expected to elicit a therapeutically tolerable weak immunogenic response in a human subject. Thus, the terms include fully humanized or fully human as well as partially humanized or partially human. If reference is made herein to use of a humanized antibody, a human antibody can be substituted or vice versa.

Humanized forms of non-human (e.g., murine) antibodies are chimeric immunoglobulins, immunoglobulin chains or fragments thereof (such as Fv, Fab, Fab', F(ab')2, or other antigen-binding subsequences of antibodies) which contain minimal sequence derived from non-human immunoglobulin. Humanized antibodies include human immunoglobulins (recipient antibody) in which residues from a complementary determining region (CDR) of the recipient are replaced by residues from a CDR of a non-human species (donor antibody) such as mouse, rat or rabbit having the desired specificity, affinity and capacity. In some instances, Fv framework residues of the human immunoglobulin are replaced by corresponding non-human residues. Humanized antibodies may also comprise residues that are found neither in the recipient antibody nor in the imported CDR or framework sequences. In general, the humanized antibody will comprise substantially all or at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region (Fc), typically that of a human immunoglobulin (Jones et al., Nature, 321:522-525 (1986); Riechmann et al., Nature, 332:323-327 (1988); and Presta, Curr. Op. Struct. Biol., 2:593-596 (1992)).

Generally, a humanized antibody has one or more amino acid residues introduced into it from a source that is non-human. These non-human amino acid residues are often referred to as import residues, which are typically taken from an import variable domain. Humanization can be essentially performed following the methods described in Jones et al., Nature, 321:522-525 (1986); Riechmann et al., Nature, 332:323-327 (1988); or Verhoeyen et al., Science, 239:1534-1536 (1988)), by substituting rodent CDRs or CDR sequences for the corresponding sequences of a human antibody. Accordingly, such humanized antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

The provided antibody or fragment can be labeled or fused with another polypeptide or fragment thereof. For example, the provided antibodies or fragments thereof can be fused with a therapeutic agent. Thus, an antibody or fragment thereof that binds to cadherin-11 may be linked to a therapeutic agent. The linkage can be covalent or noncovalent (e.g., ionic). Therapeutic agents include but are not limited to toxins, including but not limited to plant and bacterial toxins, small molecules, peptides, polypeptides and proteins. Genetically engineered fusion proteins, in which genes encoding for an antibody or fragments thereof, including the Fv region, can be fused to the genes encoding a toxin to deliver a toxin to the target cell are also provided. As used herein, a target cell or target cells are cadherin-11 positive cells, including for example, cancer cells. The antibodies taught herein can also be directly or indirectly labeled and used, for example, in diagnostic methods to detect cadherin-11.

One or more of the compounds described herein or pharmaceutically acceptable salts or prodrugs thereof can be provided in a pharmaceutical composition. Depending on the intended mode of administration, the pharmaceutical composition can be formulated in accordance with its use. The compositions will include a therapeutically effective amount of one or more of the compounds described herein or derivatives thereof in combination with a pharmaceutically acceptable carrier and, in addition, can include other agents, including other therapeutic agents. These compositions can be prepared in any manner available in the art, and can be administered in a number of ways depending on whether local or systemic treatment is desired, and on the area to be treated. Thus, the disclosed compositions can be administered, for example, orally, parenterally (e.g., intravenously), intraventricularly, intramuscularly, intraperitoneally, transdermally, extracorporeally, or topically. The compositions can be administered locally (e.g., into a tumor).

By pharmaceutically acceptable is meant a material that is not biologically or otherwise undesirable, which can be administered to an individual along with the selected compound without causing unacceptable biological effects or interacting in a deleterious manner with the other components of the pharmaceutical composition in which it is contained.

As used herein, the term carrier encompasses any excipient, diluent, filler, salt, buffer, stabilizer, solubilizer, lipid, stabilizer, or other material well known in the art for use in pharmaceutical formulations. The choice of a carrier for use in a composition will depend upon the intended route of administration for the composition. The preparation of pharmaceutically acceptable carriers and formulations containing these materials is described in, e.g., Remington's Pharmaceutical Sciences, 21st Edition, ed. University of the Sciences in Philadelphia, Lippincott, Williams & Wilkins, Philadelphia Pa., 2005. Examples of physiologically acceptable carriers include buffers such as phosphate buffers, citrate buffer, and buffers with other organic acids; antioxidants including ascorbic acid; low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as TWEEN® (ICI, Inc.; Bridgewater, N.J.), polyethylene glycol (PEG), and PLURONICS™ (BASF; Florham Park, N.J.).

Compositions containing the compound described herein or pharmaceutically acceptable salts or prodrugs thereof suitable for parenteral injection can comprise physiologically acceptable sterile aqueous or nonaqueous solutions, dispersions, suspensions or emulsions, and sterile powders for reconstitution into sterile injectable solutions or dispersions. Examples of suitable aqueous and nonaqueous carriers, diluents, solvents or vehicles include water, ethanol, polyols (propyleneglycol, polyethyleneglycol, glycerol, and the like), suitable mixtures thereof, vegetable oils (such as olive oil) and injectable organic esters such as ethyl oleate. Proper fluidity can be maintained, for example, by the use of a coating such as lecithin, by the maintenance of the required particle size in the case of dispersions and by the use of surfactants.

These compositions can also contain adjuvants such as preserving, wetting, emulsifying, and dispensing agents. Prevention of the action of microorganisms can be promoted by various antibacterial and antifungal agents, for example, parabens, chlorobutanol, phenol, sorbic acid, and the like. Isotonic agents, for example, sugars, sodium chloride, and the like can also be included. Prolonged absorption of the injectable pharmaceutical form can be brought about by the use of agents delaying absorption, for example, aluminum monostearate and gelatin.

Solid dosage forms for oral administration of the compounds described herein or pharmaceutically acceptable salts or prodrugs thereof include capsules, tablets, pills, powders, and granules. In such solid dosage forms, the compounds described herein or derivatives thereof is admixed with at least one inert customary excipient (or carrier) such as sodium citrate or dicalcium phosphate or (a) fillers or extenders, as for example, starches, lactose, sucrose, glucose, mannitol, and silicic acid, (b) binders, as for example, carboxymethylcellulose, alignates, gelatin, polyvinylpyrrolidone, sucrose, and acacia, (c) humectants, as for example, glycerol, (d) disintegrating agents, as for example, agar-agar, calcium carbonate, potato or tapioca starch, alginic acid, certain complex silicates, and sodium carbonate, (e) solution retarders, as for example, paraffin, (f) absorption accelerators, as for example, quaternary ammonium compounds, (g) wetting agents, as for example, cetyl alcohol, and glycerol monostearate, (h) adsorbents, as for example, kaolin and bentonite, and (i) lubricants, as for example, talc, calcium stearate, magnesium stearate, solid polyethylene glycols, sodium lauryl sulfate, or mixtures thereof. In the case of capsules, tablets, and pills, the dosage forms can also comprise buffering agents.

Solid compositions of a similar type can also be employed as fillers in soft and hard-filled gelatin capsules using such excipients as lactose or milk sugar as well as high molecular weight polyethyleneglycols, and the like.

Solid dosage forms such as tablets, dragees, capsules, pills, and granules can be prepared with coatings and shells, such as enteric coatings and others known in the art. They can contain opacifying agents and can also be of such composition that they release the active compound or compounds in a certain part of the intestinal tract in a delayed manner. Examples of embedding compositions that can be used are polymeric substances and waxes. The active compounds can also be in micro-encapsulated form, if appropriate, with one or more of the above-mentioned excipients.

Liquid dosage forms for oral administration of the compounds described herein or pharmaceutically acceptable salts or prodrugs thereof include pharmaceutically acceptable emulsions, solutions, suspensions, syrups, and elixirs. In addition to the active compounds, the liquid dosage forms can contain inert diluents commonly used in the art, such as water or other solvents, solubilizing agents, and emulsifiers, as for example, ethyl alcohol, isopropyl alcohol, ethyl carbonate, ethyl acetate, benzyl alcohol, benzyl benzoate, propyleneglycol, 1,3-butyleneglycol, dimethylformamide, oils, in particular, cottonseed oil, groundnut oil, corn germ oil, olive oil, castor oil, sesame oil, glycerol, tetrahydrofurfuryl alcohol, polyethyleneglycols, and fatty acid esters of sorbitan, or mixtures of these substances, and the like.

Besides such inert diluents, the composition can also include additional agents, such as wetting, emulsifying, suspending, sweetening, flavoring, or perfuming agents.

Suspensions, in addition to the active compounds, can contain additional agents, as for example, ethoxylated isostearyl alcohols, polyoxyethylene sorbitol and sorbitan esters, microcrystalline cellulose, aluminum metahydroxide, bentonite, agar-agar and tragacanth, or mixtures of these substances, and the like.

Compositions of the compounds described herein or pharmaceutically acceptable salts or prodrugs thereof for rectal administrations are optionally suppositories, which can be prepared by mixing the compounds with suitable non-irritating excipients or carriers such as cocoa butter, polyethyleneglycol or a suppository wax, which are solid at ordinary temperatures but liquid at body temperature and therefore, melt in the rectum or vaginal cavity and release the active component.

Dosage forms for topical administration of the compounds described herein or pharmaceutically acceptable salts or prodrugs thereof include ointments, powders, sprays, and inhalants. The compounds described herein or pharmaceutically salts or prodrugs thereof are admixed under sterile conditions with a physiologically acceptable carrier and any preservatives, buffers, or propellants as can be required. Ophthalmic formulations, ointments, powders, and solutions are also contemplated as being within the scope of the compositions.

The term pharmaceutically acceptable salts as used herein refers to those salts of the compound described herein or derivatives thereof that are, within the scope of sound medical judgment, suitable for use in contact with the tissues of subjects without undue toxicity, irritation, allergic response, and the like, commensurate with a reasonable benefit/risk ratio, and effective for their intended use, as well as the zwitterionic forms, where possible, of the compounds described herein. The term salts refers to the relatively non-toxic, inorganic and organic acid addition salts of the compounds described herein. These salts can be prepared in situ during the isolation and purification of the compounds or by separately reacting the purified compound in its free base form with a suitable organic or inorganic acid and isolating the salt thus formed. Representative salts include the hydrobromide, hydrochloride, sulfate, bisulfate, nitrate, acetate, oxalate, valerate, oleate, palmitate, stearate, laurate, borate, benzoate, lactate, phosphate, tosylate, citrate, maleate, fumarate, succinate, tartrate, naphthylate mesylate, glucoheptonate, lactobionate, methane sulphonate, and laurylsulphonate salts, and the like. These can include cations based on the alkali and alkaline earth metals, such as sodium, lithium, potassium, calcium, magnesium, and the like, as well as non-toxic ammonium, quaternary ammonium, and amine cations including, but not limited to ammonium, tetramethylammonium, tetraethylammonium, methylamine, dimethylamine, trimethylamine, triethylamine, ethylamine, and the like. (See Stahl and Wermuth, Pharmaceutical Salts: Properties, Selection, and Use, Wiley-VCH, 2008, which is incorporated herein by reference in its entirety, at least, for compositions taught herein.)

The compounds and derivatives thereof described herein are useful in treating cadherin-11 related diseases and conditions in humans (e.g., including pediatric and geriatric populations) and animals (e.g., veterinary applications). The methods described herein comprise administering to a subject a therapeutically effective amount of the compounds described herein or a pharmaceutically acceptable salt or prodrug thereof. Examples of cadherin-11 related diseases include rheumatoid arthritis and cancer (e.g., breast cancer, prostate cancer, glioma, glioblastoma, myeloma, leukemia, osteosarcomas, oral squamous cell cancer, renal cell cancer, colon cancer, and gastric cancer).

The methods and compounds as described herein are useful for both prophylactic and therapeutic treatment. For prophylactic use, a therapeutically effective amount of the compounds described herein or derivatives thereof are administered to a subject prior to onset (e.g., before obvious signs of a cadherin-11 related disease), during early onset (e.g., upon initial signs and symptoms of a cadherin-11 related disease), or during an established cadherin-11 related disease. Prophylactic administration can occur for several days to years prior to the manifestation of symptoms of the cadherin-11 related disease. Prophylactic administration can be used, for example, in the preventative treatment of subjects diagnosed with a genetic cadherin-11 related disease. Therapeutic treatment involves administering to a subject a therapeutically effective amount of the compounds described herein or derivatives thereof after a cadherin-11 related disease is diagnosed.

Administration of compounds described herein or pharmaceutically acceptable salts or prodrugs thereof can be carried out using therapeutically effective amounts of the compounds described herein or pharmaceutically acceptable salts or prodrugs thereof for periods of time effective to treat the cadherin-11 related disease or disorder. The effective amount of the compounds described herein or pharmaceutically acceptable salts or prodrugs thereof can be determined by one of ordinary skill in the art and includes exemplary dosage amounts for a mammal of from about 0.5 to about 200 mg/kg of body weight of active compound per day, which can be administered in a single dose or in the form of individual divided doses, such as from 1 to 4 times per day. Alternatively, the dosage amount can be from about 0.5 to about 150 mg/kg of body weight of active compound per day, about 0.5 to 100 mg/kg of body weight of active compound per day, about 0.5 to about 75 mg/kg of body weight of active compound per day, about 0.5 to about 50 mg/kg of body weight of active compound per day, about 0.5 to about 25 mg/kg of body weight of active compound per day, about 1 to about 20 mg/kg of body weight of active compound per day, about 1 to about 10 mg/kg of body weight of active compound per day, about 20 mg/kg of body weight of active compound per day, about 10 mg/kg of body weight of active compound per day, or about 5 mg/kg of body weight of active compound per day. Those of skill in the art will understand that the specific dose level and frequency of dosage for any particular subject will vary and will depend upon a variety of factors, including the activity of the specific compound employed, the metabolic stability and length of action of that compound, the species, age, body weight, general health, sex and diet of the subject, the mode and time of administration, rate of excretion, drug combination, and severity of the particular condition.

The method of treating or preventing a cadherin-11 related disease in a subject can further comprise administering to the subject a therapeutic agent or radiation therapy or a combination thereof. Thus, the provided compositions and methods can include one or more additional agents. The one or more additional agents and the compounds described herein or pharmaceutically acceptable salts or prodrugs thereof can be administered in any order, including simultaneous administration, as well as temporally spaced order of up to several days apart. The methods can also include more than a single administration of the one or more additional agents and/or the compounds described herein or pharmaceutically acceptable salts or prodrugs thereof. The administration of the one or more additional agents and the compounds described herein or pharmaceutically acceptable salts or prodrugs thereof can be by the same or different routes and concurrently or sequentially.

Therapeutic agents include but are not limited to chemotherapeutic agents, antibodies, antivirals, steroidal and non-steroidal anti-inflammatories, conventional immunotherapeutic agents, cytokines, chemokines, and/or growth factors.

The therapeutic agent can, for example, be a chemotherapeutic agent. A chemotherapeutic agent is a compound or composition effective in inhibiting or arresting the growth of an abnormally growing cell. Thus, such an agent may be used therapeutically to treat cancer as well as other diseases marked by abnormal cell growth. Illustrative examples of anti-cancer compounds include, but are not limited to, bexarotene, gefitinib, erlotinib, gemcitabine, paclitaxel, docetaxel, topotecan, irinotecan, vinorelbine, capecitabine, leucovorin, oxaliplatin, bevacizumab, cetuximab, panitumumab, bortezomib, oblimersen, hexamethylmelamine, ifosfamide, CPT-11, deflunomide, cycloheximide, dicarbazine, asparaginase, mitotant, vinblastine sulfate, carboplatin, colchicine, etoposide, melphalan, 6-mercaptopurine, teniposide, vinblastine, antibiotic derivatives (e.g. anthracyclines such as doxorubicin, liposomal doxorubicin, and diethylstilbestrol doxorubicin, bleomycin, daunorubicin, and dactinomycin); antiestrogens (e.g., tamoxifen); antimetabolites (e.g., fluorouracil (FU), 5-FU, methotrexate, floxuridine, interferon alpha-2B, glutamic acid, plicamycin, mercaptopurine, and 6-thioguanine); cytotoxic agents (e.g., carmustine, BCNU, lomustine, CCNU, cytosine arabinoside, cyclophosphamide, estramustine, hydroxyurea, procarbazine, mitomycin, busulfan, cisplatin, vincristine and vincristine sulfate); hormones (e.g., medroxyprogesterone, estramustine phosphate sodium, ethinyl estradiol, estradiol, megestrol acetate, methyltestosterone, diethylstilbestrol diphosphate, chlorotrianisene, and testolactone); nitrogen mustard derivatives (e.g., mephalen, chlorambucil, mechlorethamine (nitrogen mustard) and thiotepa); and steroids (e.g., bethamethasone sodium phosphate). Optionally, the chemotherapeutic agent is temozolomide, or carmustine.

Any of the aforementioned therapeutic agents can be used in any combination with the compositions described herein. Combinations are administered either concomitantly (e.g., as an admixture), separately but simultaneously (e.g., via separate intravenous lines into the same subject), or sequentially (e.g., one of the compounds or agents is given first followed by the second). Thus, the term combination is used to refer to concomitant, simultaneous, or sequential administration of two or more agents.

Also provided herein are kits for preventing or treating a cadherin-11 disease in a subject. A kit can include any of the compounds or compositions described herein. For example, a kit can include a compound of Formula I, Formula II, the additional cadherin-11 inhibitors described herein, or combinations thereof. A kit can further include one or more anti-inflammatory agents. A kit can also include one or more chemotherapeutic agents. A kit can include an oral formulation of any of the compounds or compositions described herein. A kit can additionally include directions for use of the kit (e.g., instructions for treating a subject). A kit can include a means of administering the compound or composition or a vessel for containing the compound or composition.

Provided herein is a method for determining whether a subject has or is at risk for developing cancer. The method includes the steps of obtaining a biological sample from the subject and determining the level of expression of cadherin-11 in the sample, wherein an increase in expression as compared to a control indicates the subject has or is at risk for developing cancer. Optionally, the cancer is renal cell cancer, prostate cancer, breast cancer, glioma, glioblastoma, myeloma, or leukemia. Optionally, the cancer exhibits morphologic and molecular changes characteristic of mesenchymal tissue (i.e., mesenchymal-like cancer) or has a basal-like phenotype (i.e., a basal-like cancer). Optionally, the cancer is metastatic or has a poor prognosis or is invasive.

An increased or higher level in expression or activity of cadherin-11 as compared to a control means that the level of expression or activity of cadherin-11 is higher in the biological sample from a subject being tested than in a control sample. As used throughout, higher or increase as compared to a control refer to increases above a control. As used herein, control refers to a reference standard from, for example, an untreated sample or subject, from a subject without cancer, an untreated subject with cancer. By way of another example, a control level can be the level of expression or activity in a control sample in the absence of a stimulus. Alternatively, a control level can be the level of expression or activity in a control sample from a subject or group of subjects without cancer. An increased or high level is optionally statistically higher than a selected control using at least one acceptable statistical analysis method.

As used herein a biological sample which is subjected to testing is a sample derived from a subject and includes, but is not limited to, any cell, tissue or biological fluid. The sample can be, but is not limited to, peripheral blood, plasma, urine, saliva, gastric secretion, feces, bone marrow specimens, primary or metastatic tumor biopsy, embedded tissue sections, frozen tissue sections, cell preparations, cytological preparations, exfoliate samples (e.g., sputum), fine needle aspirations, amnion cells, fresh tissue, dry tissue, and cultured cells or tissue. The biological sample can also be whole cells or cell organelles (e.g., nuclei). A biological sample can also include a partially purified sample, cell culture, or a cell line.

Assay techniques that can be used to determine levels of expression in a sample are well-known to those of skill in the art. Such assay methods include radioimmunoassays, reverse transcriptase PCR (RT-PCR) assays, immunohistochemistry assays, in situ hybridization assays, competitive-binding assays, Western blot analyses, ELISA assays and proteomic approaches, two-dimensional gel electrophoresis (2D electrophoresis) and non-gel based approaches such as mass spectrometry or protein interaction profiling. Assays also include, but are not limited to, competitive and non-competitive assay systems using techniques such as radioimmunoassays, enzyme immunoassays (EIA), enzyme linked immunosorbent assay (ELISA), sandwich immunoassays, precipitin reactions, gel diffusion reactions, immunodiffusion assays, agglutination assays, complement-fixation assays, immunoradiometric assays, fluorescent immunoassays, protein A immunoassays, and immunoelectrophoresis assays. For examples of immunoassay methods, see U.S. Pat. Nos. 4,845,026 and 5,006,459.

For diagnostic methods, an antigen binding partner, for example, an antibody, can be labeled with a detectable moiety and used to detect the antigen in a sample. The antibody can be directly labeled or indirectly labeled (e.g., by a secondary or tertiary antibody that is labeled with a detectable moiety). Numerous labels are available including, but not limited to radioisotopes, fluorescent labels, and enzyme-substrate labels. Radioisotopes include, for example, $^{35}S$, $^{14}C$, $^{125}I$, $^{3}H$, and $^{131}I$ Fluorescent labels include, for example, rare earth chelates (europium chelates), fluorescein and its derivatives, rhodamine and its derivatives, dansyl, Lissamine, phycoerythrin and Texas Red. The labels can be conjugated to the antigen binding partner using the techniques disclosed in Current Protocols in Immunology, Volumes 1 and 2, Coligen et al., Ed., Wiley-Interscience, New York, N.Y., Pubs., (1991), for example.

When using enzyme-substrate labels, the enzyme preferably catalyses a chemical alteration of the chromogenic substrate which can be measured using various techniques. For example, the enzyme may catalyze a color change in a substrate, which can be measured spectrophotometrically. Alternatively, the enzyme may alter the fluorescence or chemiluminescence of the substrate. The chemiluminescent substrate becomes electronically excited by a chemical reaction and may then emit light which can be measured (using a chemiluminometer, for example) or donates energy to a fluorescent acceptor. Examples of enzymatic labels include luciferases (e.g., firefly luciferase and bacterial luciferase), luciferin, 2,3-dihydrophthalazinediones, malate dehydrogenase, urease, peroxidase such as horseradish peroxidase (HRPO), alkaline phosphatase, Θ-galactosidase, glucoamylase, lysozyme, saccharide oxidases (e.g., glucose oxidase, galactose oxidase, and glucose-6-phosphate dehydrogenase), heterocyclic oxidases (such as uricase and xanthine oxidase), lactoperoxidase, microperoxidase, and the like. Techniques for conjugating enzymes are described in O'Sullivan et al., Methods for the Preparation of Enzyme-Antibody Conjugates for use in Enzyme Immunoassay, in Methods in Enzym. (ed J. Langone & H. Van Vunakis), Academic press, New York, 73: 147-166 (1981). Examples of enzyme-substrate combinations include, for example, horseradish peroxidase (HRPO) with hydrogen peroxidase as a substrate, alkaline phosphatase (AP) with para-Nitrophenyl phosphate as chromogenic substrate, and Θ-D-galactosidase (Θ-D-Gal) with a chromogenic substrate (e.g. p-nitrophenyl-Θ-D-galactosidase) or fluorogenic substrate 4-methylumbelliferyl-Θ-D-galactosidase.

In an ELISA assay, an antibody is prepared, if not readily available from a commercial source, specific to an antigen. In addition, a reporter antibody generally is prepared which binds specifically to the antigen. The reporter antibody is attached to a detectable reagent such as a radioactive, fluorescent or enzymatic reagent, for example horseradish peroxidase enzyme or alkaline phosphatase. To carry out the ELISA, antibody specific to antigen is incubated on a solid support, e.g., a polystyrene dish, that binds the antibody. Any free protein binding sites on the dish are then covered by incubating with a non-specific protein such as bovine serum albumin. Next, the sample to be analyzed is incubated in the dish, during which time the antigen binds to the specific antibody attached to the polystyrene dish. Unbound sample is washed out with buffer. A reporter antibody specifically directed to the antigen and linked to a detectable reagent such as horseradish peroxidase is placed in the dish resulting in binding of the reporter antibody to any antibody bound to the antigen. Unattached reporter antibody is then washed out. Reagents for peroxidase activity, including a colorimetric substrate are then added to the dish. Immobilized peroxidase, linked to antibodies, produces a colored reaction product. The amount of color developed in a given time period is proportional to the amount of antigen present in the sample. Quantitative results typically are obtained by reference to a standard curve.

A competition assay can also be employed wherein antibodies specific to antigen are attached to a solid support and labeled antigen and a sample derived from the subject or control are passed over the solid support. The amount of label detected which is attached to the solid support can be correlated to a quantity of antigen in the sample.

Of the proteomic approaches, 2D electrophoresis is a technique well known to those in the art. Isolation of individual proteins from a sample such as serum is accomplished using sequential separation of proteins by different characteristics usually on polyacrylamide gels. First, proteins are separated by size using an electric current. The current acts uniformly on all proteins, so smaller proteins move farther on the gel than larger proteins. The second dimension applies a current perpendicular to the first and separates proteins not on the basis of size but on the specific electric charge carried by each protein. Since no two proteins with different sequences are identical on the basis of both size and charge, the result of a 2D separation is a square gel in which each protein occupies a unique spot. Analysis of the spots with chemical or antibody probes, or subsequent protein microsequencing can reveal the relative abundance of a given protein and the identity of the proteins in the sample.

Optionally, a genetic sample from the biological sample can be obtained. The genetic sample comprises a nucleic acid, preferably RNA and/or DNA. For example, in determining the expression of genes mRNA can be obtained from the biological sample, and the mRNA may be reverse transcribed into cDNA for further analysis. Alternatively, the mRNA itself is used in determining the expression of genes.

A genetic sample may be obtained from the biological sample using any techniques known in the art (Ausubel et al. Current Protocols in Molecular Biology (John Wiley & Sons, Inc., New York, 1999); Molecular Cloning: A Laboratory Manual, 2nd Ed., ed. by Sambrook, Fritsch, and Maniatis (Cold Spring Harbor Laboratory Press: 1989); Nucleic Acid Hybridization (B. D. Hames & S. J. Higgins eds. 1984)). The nucleic acid may be purified from whole cells using DNA or RNA purification techniques. The genetic sample may also be amplified using PCR or in vivo techniques requiring subcloning. The genetic sample can be obtained by isolating mRNA from the cells of the biological sample and reverse transcribing the RNA into DNA in order to create cDNA (Khan et al. Biochem. Biophys. Acta 1423: 17 28, 1999).

Once a genetic sample has been obtained, it can be analyzed for the presence or absence of one or more particular genes encoding, for example, cadherin-11. The analysis may be performed using any techniques known in the art including, but not limited to, sequencing, PCR, RT-PCR, quantitative PCR, restriction fragment length polymorphism, hybridization techniques, Northern blot, microarray technology, DNA microarray technology, and the like. In determining the expression level of a gene or genes in a genetic sample, the level of expression may be normalized by comparison to the expression of another gene such as a well known, well characterized gene or a housekeeping gene. For example, reverse-transcriptase PCR (RT-PCR) can be used to detect the presence of a specific mRNA population in a complex mixture of thousands of other mRNA species. In RT-PCR, an mRNA species is first reverse transcribed to complementary DNA (cDNA) with use of the enzyme reverse transcriptase; the cDNA is then amplified as in a standard PCR reaction. RT-PCR can thus reveal by amplification the presence of a single species of mRNA.

Hybridization to clones or oligonucleotides arrayed on a solid support (i.e., gridding) can be used to both detect the expression of and quantitate the level of expression of that gene. In this approach, a cDNA encoding an antigen is fixed to a substrate. The substrate may be of any suitable type including but not limited to glass, nitrocellulose, nylon, or plastic. At least a portion of the DNA encoding the antigen is attached to the substrate and then incubated with the analyte, which may be RNA or a complementary DNA (cDNA) copy of the RNA, isolated from the sample of interest. Hybridization between the substrate bound DNA and the analyte can be detected and quantitated by several means including but not limited to radioactive labeling or fluorescence labeling of the analyte or a secondary molecule designed to detect the hybrid. Quantitation of the level of gene expression can be done by comparison of the intensity of the signal from the analyte compared with that determined from known standards. The standards can be obtained by in vitro transcription of the target gene, quantitating the yield, and then using that material to generate a standard curve.

As used throughout, subject can be a vertebrate, more specifically a mammal (e.g., a human, horse, cat, dog, cow, pig, sheep, goat, mouse, rabbit, rat, and guinea pig), birds, reptiles, amphibians, fish, and any other animal. The term does not denote a particular age or sex. Thus, adult and newborn subjects, whether male or female, are intended to be covered. As used herein, patient or subject may be used interchangeably and can refer to a subject with a disease or disorder (e.g., cancer). The term patient or subject includes human and veterinary subjects.

As used herein the terms treatment, treat, or treating refers to a method of reducing the effects of a disease or condition or symptom of the disease or condition. Thus in the disclosed method, treatment can refer to a 10%, 20%, 30%, 40%, 50%, 60%, 70%, 80%, 90%, or 100% reduction in the severity of an established disease or condition or one or more symptoms of the disease or condition. For example, a method for treating a disease is considered to be a treatment if there is a 10% reduction in one or more symptoms or signs (e.g., size of the tumor or rate of tumor growth) of the disease in a subject as compared to a control. Thus the reduction can be a 10%, 20%, 30%, 40%, 50%, 60%, 70%, 80%, 90%, 100%, or any percent reduction in between 10% and 100% as compared to native or control levels. It is understood that treatment does not necessarily refer to a cure or complete ablation of the disease, condition, or symptoms of the disease or condition.

As used herein, the terms prevent, preventing, and prevention of a disease or disorder refers to an action, for example, administration of a composition or therapeutic agent, that occurs before or at about the same time a subject begins to show one or more symptoms of the disease or disorder, which inhibits or delays onset or severity of one or more symptoms of the disease or disorder. As used herein, references to decreasing, reducing, or inhibiting include a change of 10%, 20%, 30%, 40%, 50%, 60%, 70%, 80%, 90% or greater as compared to a control level. Such terms can include but do not necessarily include complete elimination.

Disclosed are materials, compositions, and components that can be used for, can be used in conjunction with, can be used in preparation for, or are products of the disclosed methods and compositions. These and other materials are disclosed herein, and it is understood that when combinations, subsets, interactions, groups, etc. of these materials are disclosed that while specific reference of each various individual and collective combinations and permutations of these compounds may not be explicitly disclosed, each is specifically contemplated and described herein. For example, if a method is disclosed and discussed and a number of modifications that can be made to a number of molecules including the method are discussed, each and every combination and permutation of the method, and the modifications that are possible are specifically contemplated unless specifically indicated to the contrary. Likewise, any subset or combination of these is also specifically contemplated and disclosed. This concept applies to all aspects of this disclosure including, but not limited to, steps in methods using the disclosed compositions. Thus, if there are a variety of additional steps that can be performed, it is understood that each of these additional steps can be performed with any specific method steps or combination of method steps of the disclosed methods, and that each such combination or subset of combinations is specifically contemplated and should be considered disclosed.

Throughout this application, various publications are referenced. The disclosures of these publications in their entireties are hereby incorporated by reference into this application.

A number of aspects have been described. Nevertheless, it will be understood that various modifications may be made. Furthermore, when one characteristic or step is described it can be combined with any other characteristic or step herein even if the combination is not explicitly stated. Accordingly, other aspects are within the scope of the claims.

The examples below are intended to further illustrate certain aspects of the methods and compounds described herein, and are not intended to limit the scope of the claims.

EXAMPLES

Example 1

Cell Culture and Generation of Stable Cell Lines

Figure 2:
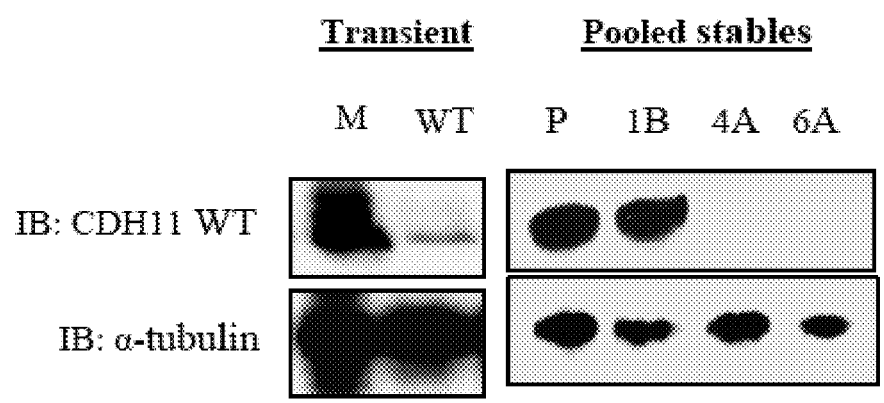
FIG. 2 shows images of the inhibition of cadherin-11 expression with RNAi in transient and pooled stables. Two independently derived cadherin-11 siRNA (6A, 4A) lines; control pooled stable cell line from a scrambled construct (1B).
Figure 3:
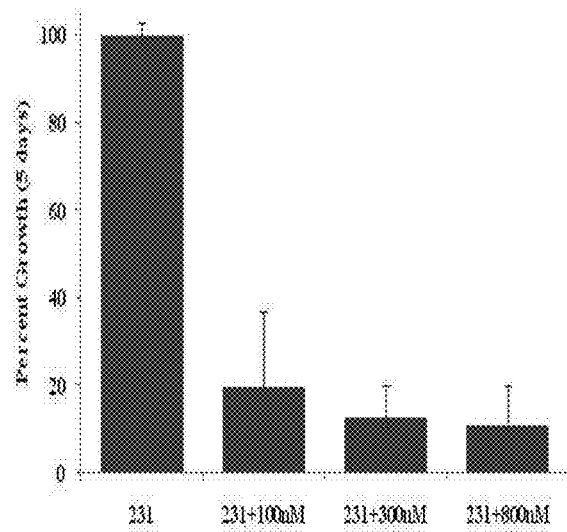
FIG. 3 is a bar graph showing the percent growth of untreated cells and cells treated with Compound 1 at concentrations of 100 nM, 300 nM, and 800 nM after five days.
Figure 4:
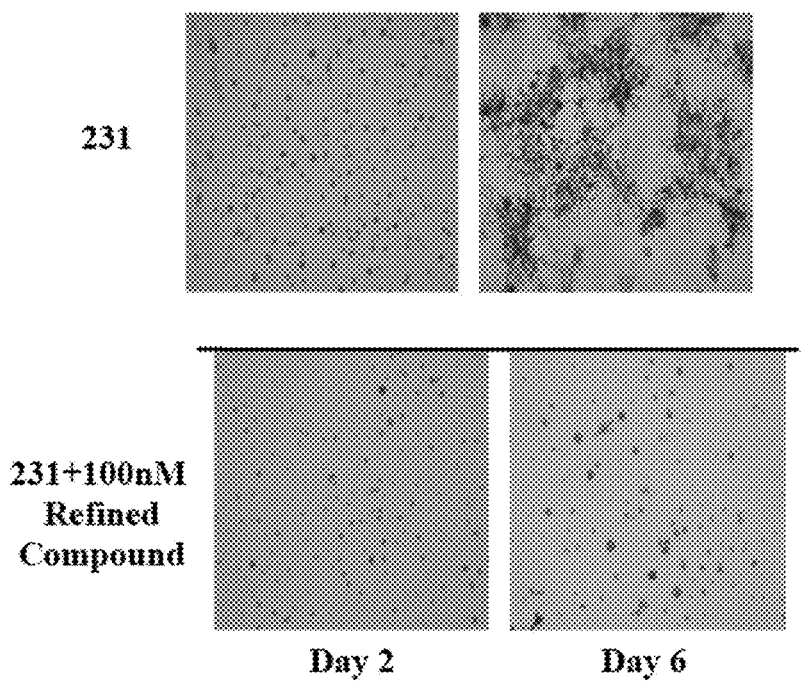
FIG. 4 shows pictures of untreated cells (231) and cells treated with 100 nM of Compound 1 (231+100 nM) after two and six days.
Figure 5:
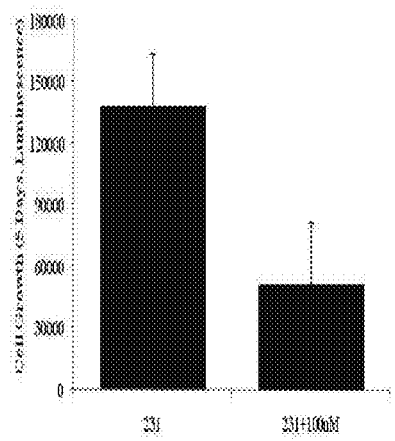
FIG. 5 is a bar graph showing the cell growth of untreated cells (231) and cells treating with 100 nM of Compound 1 (231+100 nM) after five days as measured by chemoluminescence.
Figure 6A:
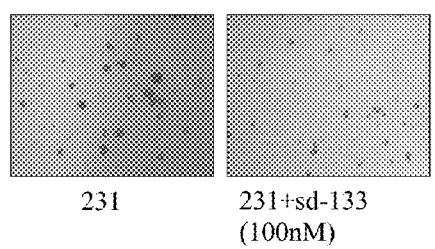
FIG. 6A shows pictures of colonies of untreated cells (231) and cells treated with 100 nM of Compound 1 (231+sd-133 (100 nM)).
Figure 6B:
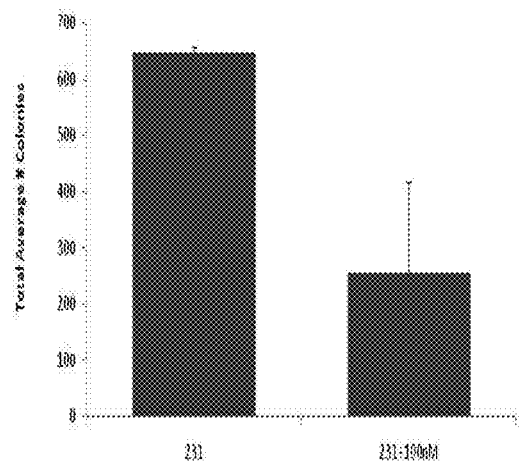
FIG. 6B is a bar graph showing the total average number of colonies in untreated cells (231) and cells treated with 100 nM of Compound 1 (231+100 nM).
Figure 7:
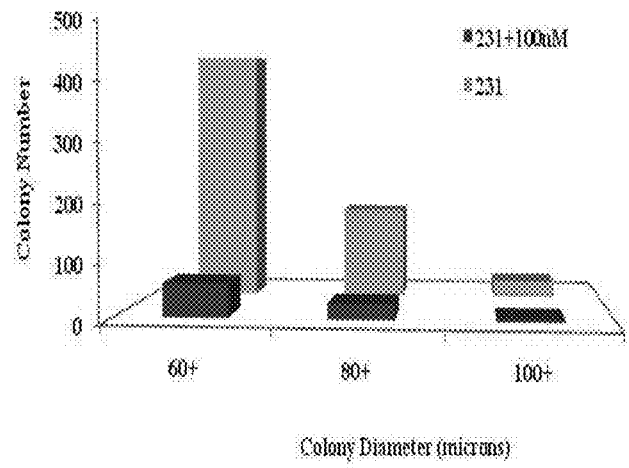
FIG. 7 is a bar graph showing the colony and size of the colony for untreated cells (231) and cells treated with 100 nM of Compound 1 (231+100 nM).
Figure 8:
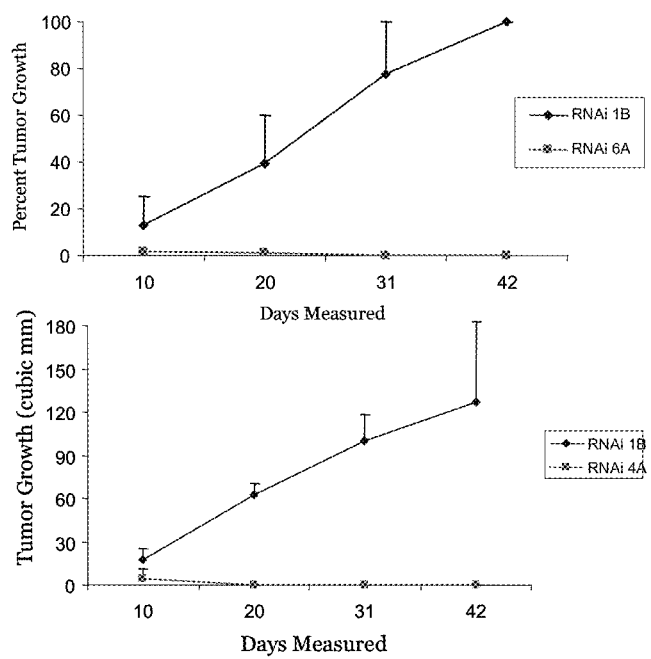
FIG. 8 shows graphs displaying the tumor growth in nude mice injected with cells expressing control siRNA (RNAi 1B) and cadherin-11 siRNA (RNAi 6A and RNAi 4A).

To investigate the specific role of cadherin-11 in breast cancer, RNA interference to knockdown endogenous cadherin-11 expression in aggressive breast and prostate cancer cells was employed. Specifically, MDA-MB-231 breast cancer cells were used for stable transfection of siRNA or infection of shRNA, along with PC-3 prostate cancer cells, targeting the wild type isoform of cadherin-11 via its intracellular domain. The siRNA target sequence was designed using a database, placed into a commercial vector, and further transfected into MDA-MB-231 cells. Transient expression of the siRNA was determined by examination of cadherin-11 protein for ample knockdown. Upon confirmation, the siRNA vector was cotransfected with a second vector, one allowing for stable selection of RNAi-containing cells, and MDA-MB-231 breast cancer cells. Selected clones were pooled, and the entire process was repeated in triplicate to obtain more homogenous pools of stable cells (FIG. 2). In addition, lentiviral particles containing two separate shRNA sequences targeting the same region of cadherin-11 were used to infect MDA-MB-231 cells, as well as PC-3 prostate cancer cells for validation in alternate cancers. Upon stable selection, single-cell cloning was employed to obtain a more pure population of testable cells. Cadherin-11 expression was determined in the resulting stable cell lines at both the RNA level by quantitative RT-PCR and protein by Western blot. Consequently, stable cells for all experiments discussed were chosen based upon immunoblot expression (see Example 2 for experimental details). Two cell lines, chosen from among the pooled siRNA-targeted stables tested, along with one clonal cell line from each of the two shRNA sequence-targeted stables created (54333 and 54334), were selected for use in these experiments based upon their favorable level of knockdown. Specifically, parental breast cancer lines (MDA-MB-231) and prostate cancer cell lines (PC-3) (American Type Culture Collection; Manassas, Va.) were maintained in Dulbecco's Modified Eagle Medium (DMEM, Invitrogen, Carlsbad, Calif.) supplemented with 5% fetal bovine serum. siRNA pooled stables were created using siRNA templates containing T7 promoter sequences at the 3' end of the sequence and an AA 5' overhang (Integrated DNA Technologies, Inc.; Coralville, Iowa), using anti-sense sequence 5'-AACAGCGTGGATGTCGATGACCCTG TCTC-3' (SEQ ID NO:1) and sense sequence 5'-AAGT-CATCGACATCCACGCT GCCTGTCTC-3' (SEQ ID NO:2) to target cadherin-11 wt isoform. Double-stranded siRNA vectors were synthesized using the Silencer™ siRNA Construction Kit (Ambion; Foster City, Calif.) and co-transfected with hygromycin B-resistant vector or vector alone into MDA-MB-231 using Fugene (Roche Diagnostics; Indianapolis, Ind.). Stable cell clones were selected using 1mg/mL Hygromycin B and maintained using 0.5 mg/mL of antibiotic. The entire transfection process was repeated three times consecutively, with stable cell clones being selected in each instance. Following final selection, five clones were selected at random and pooled to create stable cell lines for further analysis. shRNA Lentiviral stable cells were created using MISSION® shRNA lentiviral transduction particles (Sigma-Aldrich; St. Louis, Mo.) directed against human cadherin-11/OB-cadherin. Single cell clones were selected in 15 μg/mL puromycin and maintained for further analysis in 10 μg/mL antibiotic. All stable cell lines used in further studies were selected from those generated based upon cadherin-11 protein expression as measured by Western blot analysis.

Example 2

Immunoblot Assay

Confluent cells from 6-cm tissue culture dishes were isolated via scraping in RIPA lysis buffer solution consisting of RIPA, NaF, NaV, and a protease inhibitor on ice. The lysates were homogenized using a 25-gauge needle, rotated for 15 min at 4° C., and then centrifuged at 15,000 rpm for 15 min to remove insoluble material. The protein in the supernatant was quantified using a Bio-Rad DC protein assay according to supplied protocol. The protein samples were prepared in 1×LDS sample buffer and 1×DTT reducing agent and then boiled for 10 min. 30 μg protein was separated on a 3-8% Tris-Acetate NuPage gel (Novex; Carlsbad, Calif.), transferred to nitrocellulose (Millipore; Billerica, Mass.), and blocked for 1 h at room temperature in PBS-Tween supplemented with 5% milk. The blots were probed with monoclonal antibodies recognizing cadherin-11 wt (5B2H5: Zymed) and GAPDH as a loading control. A secondary peroxidase-labelled antibody (Kirkegaard and Perry Laboratories, Inc.; Gaithersburg, Md.) was used on the blots, and the resulting bands were visualized using ECL (Amersham; Amersham, UK).

Example 3

Computational Methods of Screening Small Molecule Cadherin-11 Inhibitors

Small molecule inhibitors were tested for potential use in targeted cancer therapies. A computer-based model of structural modeling was used to predict small molecules capable of binding to specific hydrophobic pockets in the cadherin-11 extracellular domain, EC1. Unlike other cadherins, cadherin-11 is found at regions of cell-extracellular matrix contact in addition to cell-cell contact sites. Consistent with this, cadherin-11 possesses a site in EC1 similar to the matrix-interacting site of integrins, and the cadherin-11 splice variant is sequestered in the extracellular matrix. The crystal structure of cadherin-11 was recently solved and confirmed that the region targeted by the first generation blockers is not involved in cell-cell interactions and revealed two other potential sites for interference of cell-cell adhesion. This structure was used as a basis for docking molecular simulations and the production of pharmacophores designed to block one or both of the two adjacent regions (P1 and P2), which are necessary for cadherin-11 function in cell-cell adhesion.

Tryptophan binding pockets of the first extracellular (EC1) domain of cadherin-11 (type 2) and N-cadherin (type 1) were compared and a flexible in-silico screening approach was utilized to include flexibility in the EC1 structure homo- and hetero dimer interface. Ensembles of structures and molecular dynamics (MD) snapshots were generated. Their subsets of representative conformations were used for docking simulations to explore the conformational flexibility of the protein and the induced-fit effect of the protein-ligand interactions to a greater extent. The "best fit" compounds were selected based on the scoring functions followed by our optimal reference binding mode (ORBM) approach and functionally tested in subsequent assays.

Example 4

Immunofluorescence

Cadherin-11 localization in the cell was also observed for each cell line using immunofluorescence. Cells were grown on 18-mm coverslips, fixed and permeabilized using cold methanol at −20° C. for 15 min, and blocked in 6% goat serum for 1 h at room temperature. Coverslips were incubated with primary antibody (5B2H5: cadherin-11 monoconal antibody, and SHB7: beta-catenin polyclonal antibody) overnight at 4° C. Coverslips were washed and incubated with Fluorescein (Kirkegaard and Perry Laboratories, Inc.; Gaithersburg, Md.) or Texas Red-conjugated (Jackson ImmunoResearch Laboratories, Inc.; West Grove, Pa.) secondary antibody for 1 h at room temperature. Coverslips were washed and mounted using Vectashield fluorescence mounting medium and visualized with a Nikon 6000 fluorescent microscope.

Cadherin-11 is a transmembrane glycoprotein that works through the formation of adherens junctions, and thus logically resides at the cell membrane. It was found that cadherin-11 expression was significantly reduced in the cell lines containing RNAi with cadherin-11 targeted sequences, as compared to those possessing RNAi with a scrambled sequence or empty vector. Furthermore, cadherin-11 was localized at the cell membrane in the stable lines albeit minimally in RNAi-targeted cells. Also examined were p120 and beta-catenin levels in the stable cell lines. Beta-catenin expression remained relatively constant among all cell lines, and its location was retained at the cell membrane. Morphology of the stable cell lines closely mimicked that of parental MDA-MB-231 cells.

Example 5

Proliferation Assays

Cell adhesion affects cellular proliferation throughout development and in tumorigenesis. The exogenous expression of cadherin-11 in SKBR3 breast cancer cells resulted in only a mild, non-significant increase in proliferation. However, knockdown of endogenous cadherin-11 in smooth muscle cells significantly inhibited their proliferation. It was investigated how the reduction of cadherin-11 in MDA-MB-231 breast cancer and PC-3 prostate cancer cells would affect their proliferative ability.

For crystal violet assays, cells were plated in triplicate in 96-well tissue culture dishes at 4 separate densities. Cells were grown in DMEM supplemented with 5% fetal bovine serum for a period of 5 days. Dishes representing growth were stained with crystal violet on Days 1, 3 and 5 after plating, by removing growth medium, staining with 50 μL of crystal violet stain for 10 min, then gently washing in dH$_2$O and allowing to dry overnight. Stained cells were solubilized in 100 μL 50/50 (v/v) 0.1M sodium citrate and ethanol for 15 min, and absorbance was read at 630λ.

For luminescence, the cells were plated in triplicate in 24-well white-walled tissue culture dishes (Wallac; Waltham, Mass.) and grown in DMEM supplemented with 5% fetal bovine serum for 5 days. On the fifth day, the cells were resuspended in an equal volume of Cell-Titer-Glo Luminescence Reagent (Promega; Madison, Wis.), which measures ATP, and incubated for 20 min at room temperature. The assay was measured using luminescence.

Cadherin-11 knockdown yielded significant decreases in the ability of the cells to proliferate on plastic, as measured by crystal violet and a fluorescent growth reagent. The assays were statistically repeatable and show that cadherin-11 may play a role in breast cancer growth.

Example 6

Soft Agar Assays

To further characterize proliferative ability of cancer cells lacking cadherin-11, anchorage independent growth was studied in the stable cell lines. 6-well tissue culture dishes were coated with 1.2 mL 0.6% Bacto-agar (Difco; Franklin Lakes, N.J.) in DMEM supplemented with 5% fetal bovine serum. Once set, the cells were plated in triplicate in 0.3% agar (15,000/1 mL in each well) and layered gently on top of the coated agar. The plates were incubated for 10 days to 2 weeks prior to reading using a colony counter (Omnicon; Manassas, Va.) and visualized using a SMZ-1500 stereoscope (Nikon; Tokyo, JP).

For luminescence, the cells were plated in triplicate in 24-well white-walled tissue culture dishes (Wallac; Waltham, Mass.) as described above. On the final day, cells were resuspended in an equal volume of Cell-Titer-Glo Luminescence Reagent (Promega; Madison, Wis.), which measures ATP, and incubated for 20 min at room temperature. The assay was measured using luminescence.

Colony growth was observed and quantitated using a colony counter and confirmed using a fluorescent growth reagent. Correspondingly, growth differences in soft agar exist among MDA-MB-231 cells and PC-3 upon stable reduction of cadherin-11. Breast cancer cells expressing little to no cadherin-11 exhibited diminished colony formation in soft agar, which indicated an overall decrease in tumorigenic capability of the breast cancer cells. The assays were repeatable in PC-3 prostate cancer cells, which demonstrates the dominance of cadherin-11 among alternate cadherins expressed in these cells. Collectively, the growth studies in aggressive breast cancer cells show that adhesion molecule cadherin-11 is required for malignant growth of MDA-MB-231 cells.

Example 7

Wound Healing Assays and Time-lapse Imaging

Throughout development, various cadherins are expressed to direct cell specific differentiation. Cadherin expression in a given tissue dictates its fate, a phenomenon dually observed in cancer. Cadherins specifically regulate migration of developing cells, and knocking down cadherin-11 in mature smooth muscle cells or cranial neural crest cells inhibits their migratory ability. It is thought that malignant cells enhance or repress expression of certain cadherins as to promote tumorigenicity as well as metastatic potential of the tumor, for which invasive ability is essential. Upon addition of exogenous cadherin-11, non-metastatic SKBR3 breast cancer cells demonstrated a significant increase in migratory potential and invasion. To further characterize the stable cell lines, wound healing assays were performed to observe migration propensity of MDA-MB-231 breast cancer cells and PC-3 prostate cancer cells with depleted cadherin-11 expression.

The cells were plated in triplicate in 24-well tissue culture dishes and grown to confluency in DMEM supplemented with 5% fetal bovine serum. The cells were washed with 1×PBS, vertical wounds were made in each well using a 10 µL pipette tip, then growth medium was replaced. Images were recorded using an Eclipse TE-300 inverted microscope (Nikon; Tokyo, JP) equipped with motorized stage, heated and $CO_2$— regulated incubator. Phase contrast images were taken every 1 h overnight. The migration distances were calculated by manually scaling of the wound width.

Reduction of cadherin-11 in highly metastatic MDA-MB-231 breast cancer and PC-3 prostate cancer cells produced significant decreases in their migration activity. Stable knockdown cells containing some detectable cadherin-11, albeit marginal (pooled RNAi 4A), displayed better migratory ability than those with minimal to no traceable expression, further implicating cadherin-11 responsibility for the observed phenotype. Altogether, these data show that cadherin-11 aids cancer cells' ability to migrate.

Example 8

Matrigel Outgrowth Assays

Upon finding significant differences in growth and migration in cancer cells with reduced cadherin-11 expression, invasive capability of the stable cell lines was explored in a 3-dimensional matrix. The cells were plated in duplicate in a 12-well glass-bottom dish (MatTek; Ashland, Mass.) coated with 150 µL of Matrigel (BD Biosciences; San Jose, Calif.). The cells (5,000 cells/100 µl medium) were gently plated on top of the Matrigel layer directly and incubated 30 min at 37° C. Growth medium (1 mL) was gently added to each well, and growth was visualized using a 5× objective on an AH2 Vanox inverted microscope (Olympus; Tokyo, JP) equipped with a CCD camera.

MDA-MB-231 breast cancer cells form branched networks when cultured on a Matrigel basement membrane-like matrix. It was observed that control stable cells, either empty vector or scrambled target sequence, grew in a branched pattern through Matrigel mimicking their parental cell line. Stable cells with decreased cadherin-11 expression also spread in a pattern similar to control and parental cell lines, however their rate of growth was greatly delayed. Control cells form branched networks approximately 50% faster than their knockdown counterparts. These data show that while cadherin-11 is not necessary for invasion of MDA-MB-231 breast cancer cells, it is necessary for proper malignant growth.

Example 9

Animal Studies

MDA-MB-231 cells are an aggressive line and readily form tumors in nude mice. After observing significant growth differences among stable cell lines in various assays in vitro, the translational continuity of these observations in xenografts was investigated. To that end, the stable cells were subcutaneously injected into athymic nude mice at four ventral sites such that each mouse contained at least one control cell line and two knockdowns in each representative position. Tumor growth was assessed twice weekly with calipers for a minimum period of 6 weeks. The pooled stable cells containing the siRNA target sequence against cadherin-11 failed to form tumors completely in nude mice, whereas the empty vector controls formed subcutaneous tumors as expected. This result was repeatable and sustainable for more than four months. Likewise, stable cell lines containing shRNA target sequences displayed a significant delay to onset of tumor growth as compared to empty vector or scrambled sequence controls. This result was also repeatable. After about one month, subcutaneous tumors began to form from the lentivirally-infected shRNA stable cells. Once they appeared, these tumors progressed at similar rate to their empty vector and scramble sequence controls. This is likely due to the absence of selection media in vivo. For confirmation, in vitro passaging of cells in low dose selection media was done and yielded return of cadherin-11 expression to that of controls within six to eight weeks of culture. These data, along with the functional assays, show cadherin-11 is necessary for tumor growth of breast cancer cells.

The mice (female athymic mice used prior to 20 weeks of age) were maintained at the Department of Comparative Medicine Animal Facility of Georgetown University Medical Center (Washington, D.C.). Experimental procedures and handling were performed in a laminar flow hood for nude mice. For xenografts, $1-2 \times 10^6$ siRNA pooled or shRNA lentiviral stable cells, previously described, were injected s.c. into one of four mammary fat pads such that control and RNAi-expressing cells were present in the same animal. Tumors were detected by palpation and measured twice weekly with calipers, and tumor volume was deduced using the formula D1×D2×D3, where D1 is the length, D2 is the width, and D3 is the depth of the tumor. Experiments were repeated three times for all cell lines.

Example 10

Microarray Analysis

Microarray analysis has become a tool for determining potential genetic signatures of various disease profiles. In cancer, microarray has been used to analyze genetic differences regarding hormone status, cellular subtype, metastasis and recurrence, patient prognosis, and treatment response among a multitude of malignancies, tumor cells and cellular manipulations. Much of this data is available for further interpretation, leading to additional scientific conclusions from the same data sets. As such, microarray analysis was performed using the siRNA pooled stable cells to determine which genes are significantly altered upon depletion of cadherin-11 in aggressive breast cancer cells. The information generated from that analysis was further compared with existing data sets examining basal-like cancer phenotype, stromal contribution to tumor progression, metastasis, and glioblastoma multiforme. Cadherin-11 was significantly upregulated in Basal B cancer cells, poor prognosis breast and brain carcinomas and breast tumor stroma as compared with normal mammary stroma.

Example 11

Inhibition of Cadherin-11 Function

Upon initial screening of inhibitors as described in Example 3, Compound 9 (Sd-Cad11-037) and Compound 10 (Sd-Cad11-073) were found to functionally block cadherin-11 at doses of nanomolar range. These two pharmacophores were further refined and screened again to maximize solubility and then retested using various in vitro assays. Compound 1 (Sd-Cad11-133, also referred to as sd-133) significantly blocked cadherin-11 function regarding proliferation, colony growth, and invasion at 100 nanomolar range (FIGS. 3-8 and 9B). In addition, the inhibitor appears to be specific for cadherin-11, as it fails to block proliferation and invasion in MDA-MB-435 melanoma cells or MCF7 breast cancer cells at 1 and 10 μM concentrations. The data also implies that growth phenotypes in PC-3 prostate cancer cells may also be partially inhibited, further confirming that cadherin-11 is being successfully targeted by the agent. Finally, it was also observed that the compound was not cytotoxic up to a 100 μM dosage in vitro, as well as a pilot study in nude mice.

Example 12

Cadherin-11 Regulated Tumor Growth and Progression in Poor Prognosis Cancer

Materials and Methods

Cell Culture and Generation of Stable Cell Lines. Parental MDA-MB-231 breast cancer cell lines, PC-3 prostate cancer cell lines, and LN229 glioblastoma cell lines were acquired from Lombardi Comprehensive Cancer Center Tissue Culture Shared Resource (Washington, D.C.), and generated stable cell lines were maintained in DMEM (Invitrogen; Carlsbad, Calif.) supplemented with 5% fetal bovine serum (FBS) as described in Example 1. siRNA vectors were synthesized using the Silencer™ siRNA Construction Kit (Ambion; Foster City, Calif.) and co-transfected with hygromycin B-resistant vector or vector alone into MDA-MB-231 using Fugene (Roche Diagnostics; Indianapolis, Ind.). siRNA stable lines were created using anti-sense (5'-AACA-GCGTGGATGTCGATGACCCTGTCT C-3') (SEQ ID NO: 1) and sense (5'-AAGTCATCGACATCCACGCTGCCT-GTCTC-3') (SEQ ID NO: 2) sequences to target cadherin-11 (CDH11) wt. Clones were selected using lmg/mL hygromycin B and maintained using 0.5 mg/mL. The entire transfection process was repeated three times consecutively. Following final selection, five clones were randomly selected and pooled to create stable cell lines.

shRNA stable cell lines were created using MISSION® shRNA lentiviral transduction particles (Sigma-Aldrich; St. Louis, Mo.) directed against human cadherin-11 (CDH11). Two separate shRNA sequences targeting the same cadherin-11 (CDH11) region were used to infect MDA-MB-231 breast cancer cells, PC-3 prostate cancer cells, and LN229 glioblastoma cells. Clones were selected with 15 μg/mL puromycin and maintained in 10 μg/mL. Stable cell lines studied were selected based upon cadherin-11 (CDH11) protein expression as measured by Western blot analysis.

Western Blot and Immunocytochemistry. Western blots and immunocytochemistry were performed as described in Examples 2 and 4 using monoclonal antibodies to cadherin-11 (CDH11) (5B2H5: Zymed) and GAPDH (Research Diagnostics; Concord, Mass.), polyclonal β-catenin, and peroxidase, fluorescein (Kirkegaard and Perry Laboratories, Inc.; Gaithersburg, Md.) or Texas Red-conjugated (Jackson ImmunoResearch Laboratories, Inc.; West Grove, Pa.) secondary antibodies.

Proliferation Assays

Crystal Violet Assays: Cells were plated in triplicate at four separate densities and grown in DMEM with 5% FBS for five days. Cells were stained with crystal violet on days 1, 3, and 5 after plating, as described in Example 5.

Absorbance was read at 630 k using a BioRad Ultramark Microplate Imaging System with Microplate Manager 5.1 software.

Luminescence: Cells were plated in triplicate in white-walled dishes (Wallac; Waltham, Mass.) and grown in DMEM with 5% FBS for five days. At day 5, cells and a blank were resuspended in Cell-Titer-Glo Luminescence Reagent (Promega; Madison, Wis.), incubated for 20 minutes at room temperature, and measured using a Wallac Victor 2, 1420 Multilabel counter.

Soft Agar Assays. Cells (5,000) were plated in 0.3% agar layered on top of 0.6% agar in 35-mm² plates. After 2 weeks, the colonies were counted in an Omnicon 3600 automated colony counter (BioLogics, Inc.; Manassas, Va.) and visualized using a SMZ-1500 stereoscope (Nikon; Tokyo, JP). Confirmation assays were completed in 24-well dishes and analyzed using Cell-Titer-Glo Reagent (see proliferation assays).

Wound Healing and Matrigel Outgrowth Assays. Cells were grown to confluency in DMEM supplemented with 5% FBS and washed with 1×PBS. Vertical scrape wounds were made in each well (24-well plate) with a 10 µL pipette tip and then the growth medium was replaced. Phase images were recorded immediately following scraping and every hour using 10× objective (Nikon Eclipse TE-300 inverted microscope with motorized stage and $CO_2$-regulated chamber, controlled by the Multidimensional Analysis tool of Metamorph Image Acquisitions software; Tokyo, JP). Migration distances were manually calculated by caliper scaling of wound width using Metamorph tracking module.

Matrigel Outgrowth Assays: Cells (5,000 cells/100 µl medium) were plated atop 150 µL layer of Matrigel (BD Biosciences; San Jose, Calif.) in duplicate in 12-well glass-bottom dishes (MatTek; Ashland, Mass.) and incubated for 30 minutes at 37° C. Growth medium (1 mL) was gently added to each well. Growth was visualized using a 5× objective on AH2 Vanox inverted microscope (Olympus; Tokyo, JP).

Animal Studies. Female Athymic Nude Mice were Purchased from Charles River Laboratories (Wilmington, Mass.) and used prior to 20 weeks old. For xenografts, $1$-$2 \times 10^6$ stable cells were injected s.c. into one of four ventral side mammary fat pads such that each animal possessed control and RNAi-expressing cells. Tumors were measured with calipers twice per week and the tumor volume was calculated using formula D1×D2×D3 (D1=length, D2=width, D3=depth of tumor). Experiments were repeated three times for all cell lines (total 26 mice across all studies).

Statistical Methods. Student's t-test determined statistical significance for in vitro comparisons. Survival, relapse, and tumor latency analyses were plotted using Kaplan-Meier methods and compared using log-rank tests. For all statistical analyses, $p<0.05$ was considered significant. Figure columns and bars represent mean comparisons and SEM, respectively.

Microarray Analysis and Data Processing. Total RNA was isolated from knockdown and control cells [3 controls (1B), 2 each (4A and 6A knockdown)] using Trizol reagent (GIBCO BRL Life Technologies; Carlsbad, Calif.) and purified using RNeasy Mini Kit (Qiagen; Germantown, Md.). Preparation of in vitro transcription (IVT) products, oligonucleotide array hybridization, and scanning were performed (Affymetrix, Inc.; Santa Clara, Calif.). The integrity and quality of produced cRNA met recommended specifications for use with Human Genome U133-A arrays. Probe set-based gene expression measurements were generated from quantified Affymetrix image files (.CEL) using the RMA algorithm from BioConductor in BRB-Array Tools (NCI; Bethesda, Md.). Probe sets were annotated (Unigene; Fairfield, N.J.), gene expression values centered, and data organized using hierarchical clustering for similarity/difference in gene expression across samples. Analyses were restricted to genes differentially expressed in pair-wise comparisons between treated and untreated samples ($p<0.01$), resulting in 236 probe sets corresponding to 187 unigenes. Agglomerative clustering with complete linkage was applied to probe sets and samples (uncentered Pearson's correlation), and clusters visualized with Java TreeView.

Computational Methods. The energy minimized x-ray crystal structure of the EC1 domain of cadherin-11 (CDH11) dimer (PDB: 2A4C) was used for all the computational modeling. Flexible receptor structures were generated by Molecular dynamics (MD) simulations, performed with a distant-dependent dielectric constant using the Sander module of AMBER 9.0 with the PARM98 force-field parameter (all other parameters set to default). Docking simulations were done with FlexX module of Sybyl 8.0 (Tripos Inc.; St. Louis, Mo.), with parameters set to default (number of ligand conformations was set to 90) to provide a large window of flexibility to select the best fit ligand in the ORI method. 3D-pharmacophore models were developed using the UNITY module of Sybyl 8.0 (Tripos Inc.; St. Louis, Mo.). For the generation of flexible receptor conformations, molecular dynamics (MD) simulations were carried out at one nanosecond intervals, and several instantaneous low and high energy conformations were selected. These conformations were then clustered, and five representative conformations selected. In the pharmacophore strategy, several models were developed within the tryptophan binding site of the cadherin-11 EC1 domain. The representative structures obtained from the ensembles were used to develop dynamic pharmacophore models, in which the relative positions of the donor, acceptor, hydrophobic, and negative/positive centers of the residues were defined with various macro, spatial and distance constraints features with excluded volume spheres. Induced fit effect and virtual binding affinity was predicted from the 250 picosecond free energy simulations. MM-PBSA free energy method was used to predict the absolute binding affinities. Three separate simulations were carried out for ligand alone, receptor alone, and the complex. In the MM-PBSA method, the average total free energy of the system (AG) is evaluated as follows:

$$\Delta G_{bind} = <\Delta G_{complex}> - <\Delta G_{protein}> - <\Delta G_{ligand}>;$$
$$\Delta G_{bind} = <\Delta E_{MM}> + <\Delta G_{PB}> + <\Delta G_{SA}> - <T\Delta S>$$

where $\Delta G_{PB}$=polar solvation energy in continuum solvent computed using a finite-difference Poisson-Boltzmann (PB) model and $\Delta G_{SA}$=nonpolar solvation energy, obtained from the solvent-accessible surface area (SASA). The non-polar contribution to the solvation free energy was approximated with the SASA model, where surface tension coefficient=0.00202 kcal/mol Å² and β=0.92 kcal/mol. The SASA was estimated with a 1.4 Å solvent-probe radius as implemented in Sander Module of AMBER9.0. $\Delta E_{MM}$ denotes the sum of molecular mechanical (MM) energies of the molecules from internal, electrostatic, and van der Waals energies. The last term in equation is the solute entropy i.e. conformational free energy and can be estimated by normal-mode analysis.

Figure 9A:
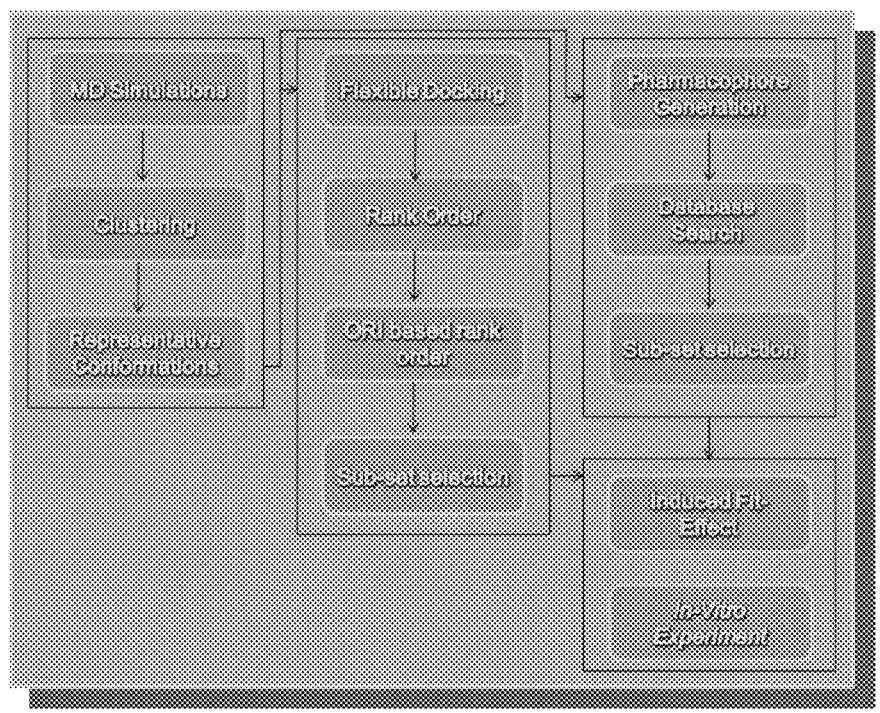
FIG. 9A is a schematic of the small molecule screening strategy described in the examples below.
Figure 9B:
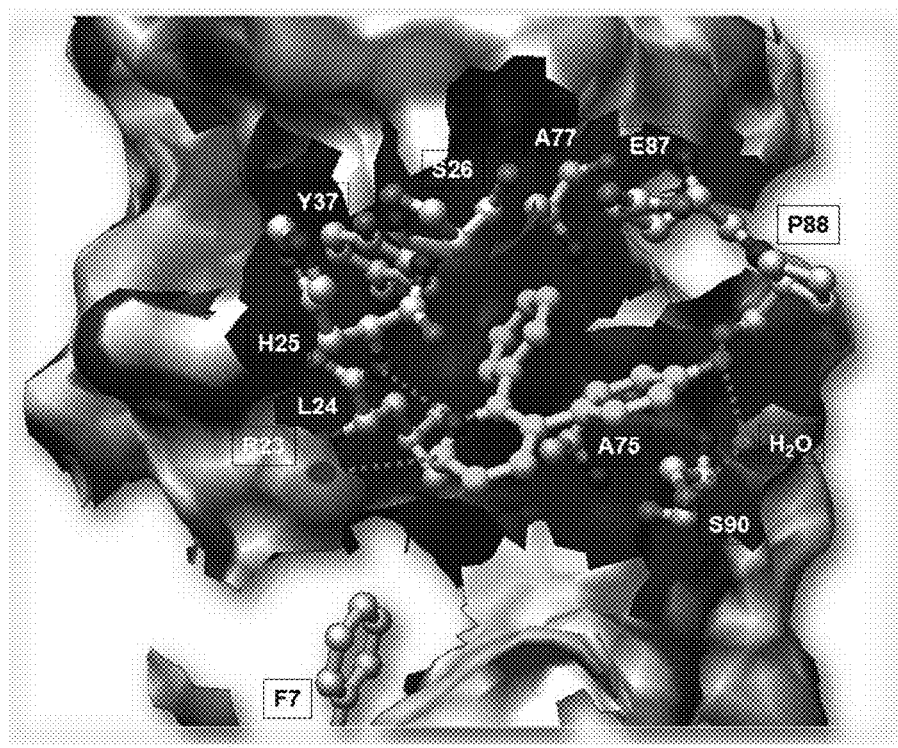
FIG. 9B is a schematic of the structural model of Compound 1 with cadherin-11.

FIG. 9A is a schematic of the small molecule screening strategy used herein. Specifically, a total of 7,073 compounds were obtained upon screening of five pharmacophore models with an in-house database of over 30 million compounds (collected from more than 150 chemical companies, and literature resources). Subsequently, 16 subsets of compounds were selected using Physical Chemical Filtering by Rule of Five, drug likeness, and commercial availability. For the small molecule docking simulations, some 157,217 pre-selected compounds (filtered for drug-likeness and commercial availability) were screened against five representative flexible conformations, including the rigid x-ray structure, and a large window of 4,546 compounds were selected based on ranking with an arbitrary energy cut-off of 25 kcal/mol. In certain cases, compounds were returned possessing a large binding free energy that would not necessarily be expected to be active. Therefore, to avoid this computational artifact, and also to reduce the large dataset, the Optimal Reference Interaction (ORI) method was implemented. The principle idea of the ORI maintains that ligands that interact with the same binding site residues as the reference molecule (in this case the tryptophan-containing pocket amino acids) are more likely to be active. The nature of the interactions and their interacting residue motifs were given as input to the ORI algorithms, and yielded 138 compounds that perfectly matched the criteria. Of the 154 compounds filtered from both strategies, the 29 most promising candidates were subjected to free energy simulations at 100 picosecond intervals, taking into consideration the induced fit effect, which accounts for conformation flexibility both before and after binding/docking simulations. In the ORI method, as well as for pharmacophore generation, all critical interactions between tryptophan and the cadherin-11 EC1 domain were included, except E87 and D27 as they showed high flexibility when exposed to solvent.

Results

Figure 10A:
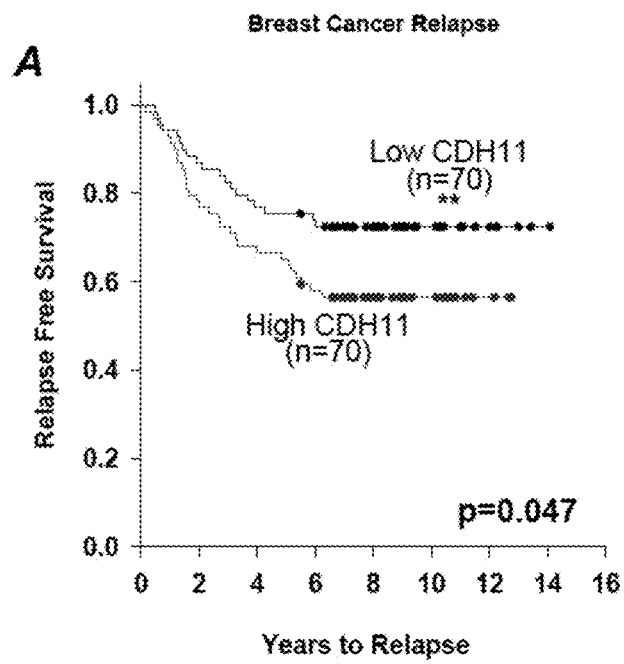
FIGS. 10A-C show graphs of Kaplan-Meier survival curves showing the correlation of cadherin-11 (CDH11) expression with clinical outcome in poor prognosis cancers. Kaplan-Meier survival curves of breast (A), prostate (B), and glioblastoma (C) patients (log-rank test p<0.05) are provided.
Figure 10B:
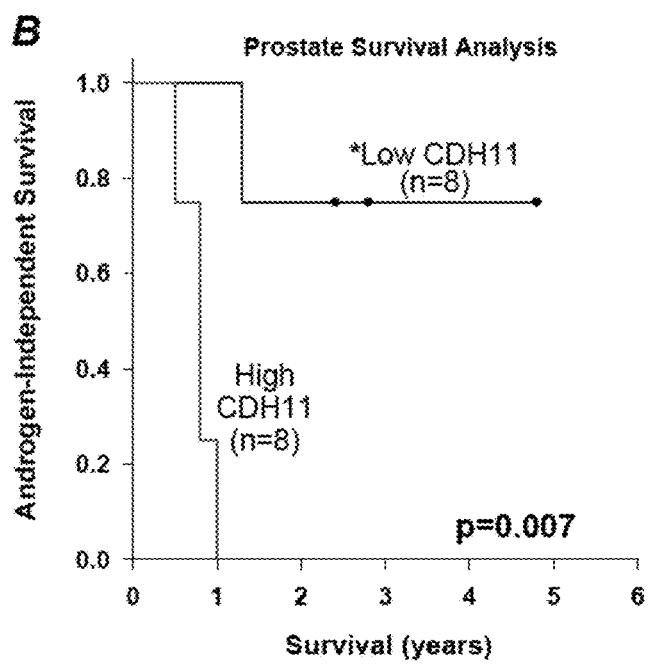
Figure 10C:
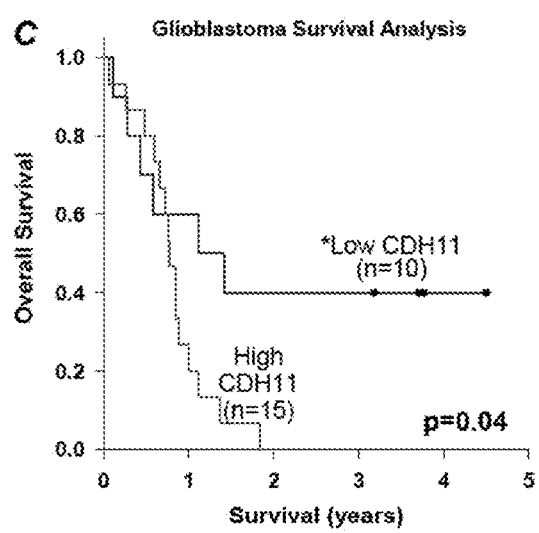

Cadherin-11 Expression is Inversely Related to Relapse and Survival in Several Cancers. Published expression array datasets examining a variety of tumor types were compared (FIG. 10). It was found that high cadherin-11 expression was significantly associated with poor outcome in breast and prostate cancer, papillary renal cell carcinoma, multiple myeloma and glioblastoma. In breast cancer cell lines, cadherin-11 expression was almost completely restricted to basal-B type cells.

Figure 11A:
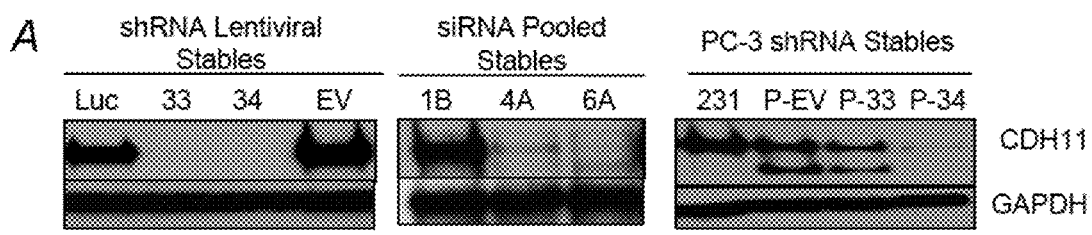
FIG. 11A is a Western blot of cadherin-11 (CDH11) in MDA-MB-231 cells stably expressing cadherin-11 shRNA (33 or 34 clonal cells) or siRNA (4A or 6A pooled cell lines), and PC-3 cells containing the same shRNA, along with empty vector (EV or 1B, respectively) or scrambled (Luc) controls. GAPDH was used as a loading control.
Figure 17A:
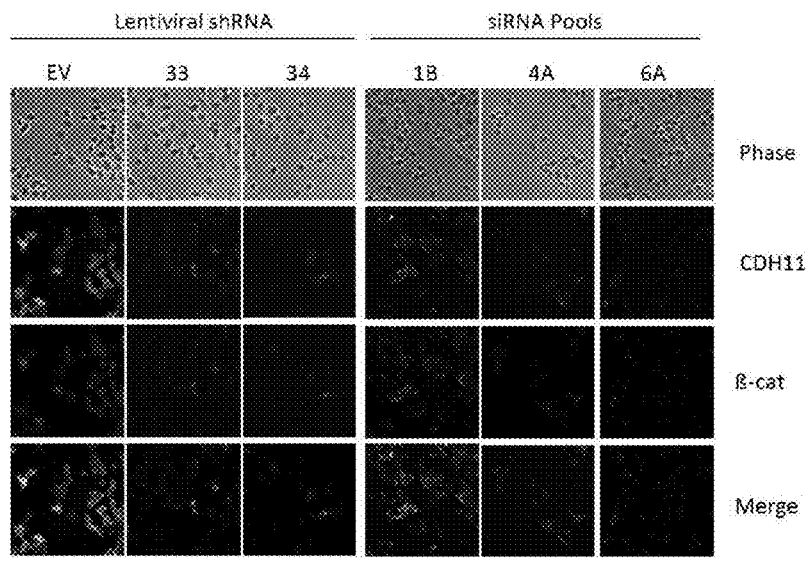
FIG. 17A shows pictures of cells expressing cadherin-11 or beta-catenin.

Cadherin-11 Regulates Proliferation and Anchorage-Independent Growth of Breast and Prostate Cancer Cells. These analyses show cadherin-11 as a useful diagnostic marker. Endogenous cadherin-11 expression in MDA-MB-231 breast and PC-3 prostate cancer cells was knocked down by stable transfection of siRNA or infection of shRNA (see Materials and Methods). Cadherin-11 expression was determined in resulting stable cell lines by quantitative RT-PCR and Western blot (FIG. 11A). Two pooled siRNA-targeted lines and one clonal line from each of two shRNA-targets (54333 and 54334) were selected. Additionally, 54333 and 54334 shRNA viral supernatants and an empty vector control were used to create stable cadherin-11-targeted PC-3 prostate cancer cells (FIG. 11A). In PC-3 cells, 54333 shRNA infection did not significantly reduce cadherin-11 and was subsequently used as a control in some experiments. Although expression was significantly reduced, cadherin-11 knockdown cell lines show similar morphology to parental MDA-MB-231 cells (FIG. 17A). β-catenin expression remained relatively constant and its location was retained at the cell membrane in the absence of cadherin-11.

Figure 11B:
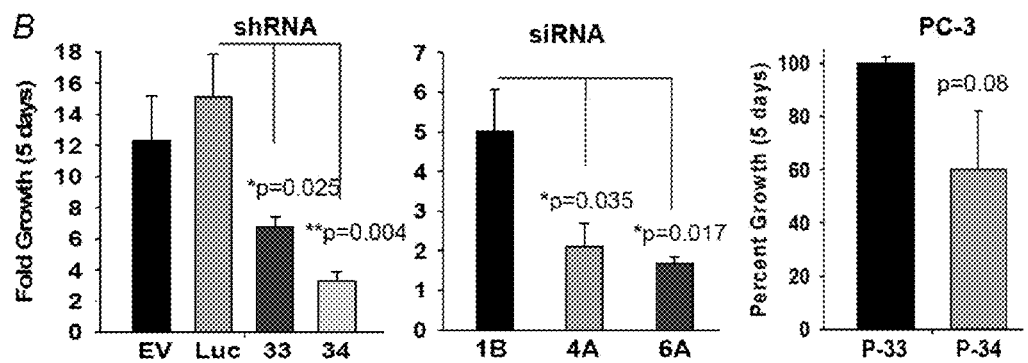
FIG. 11B is a graph showing the effect of cadherin-11 depletion on proliferation on shRNA, siRNA, and PC-3 cells measured using crystal violet staining after 5 days.
Figure 11C:
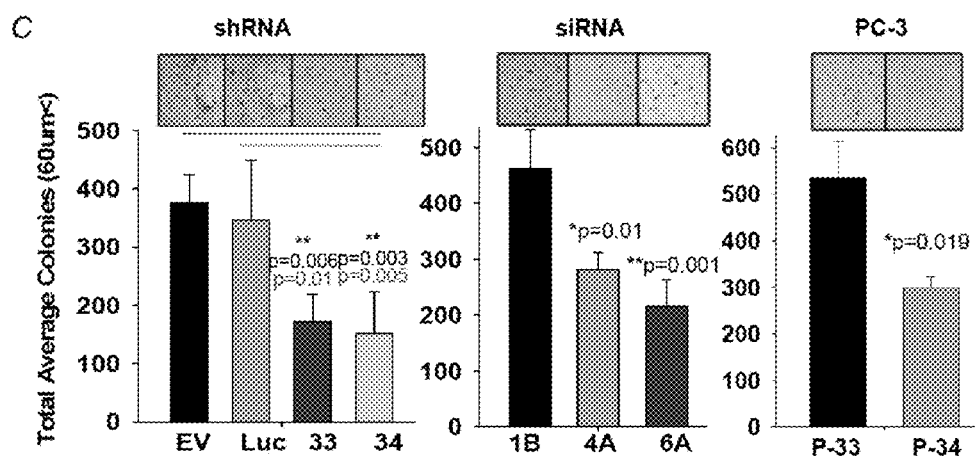
FIG. 11C is a graph showing the effect of cadherin-11 depletion on anchorage-independent colony formation in soft agar and also phase images of colony formation using a 4× objective on a Zeiss inverted microscope. Columns and bars show the mean and SEM, respectively.
Figure 17B:
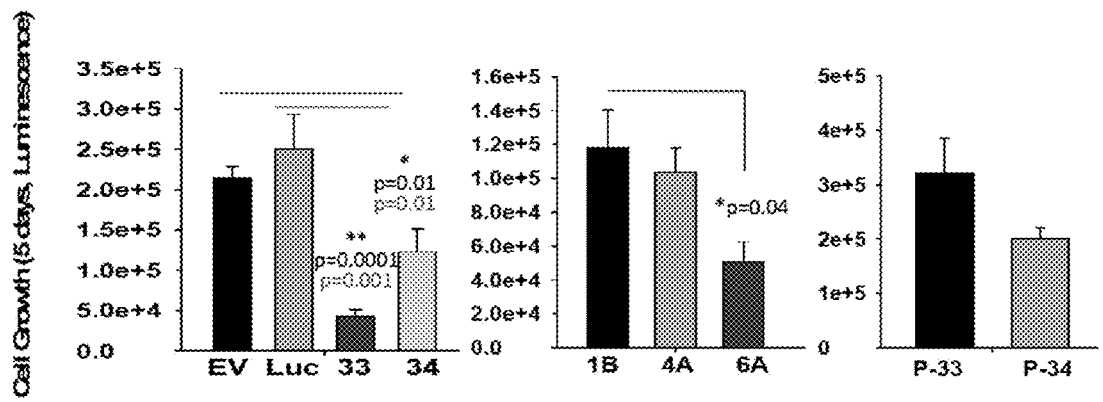
FIG. 17B shows graphs of the effect of cadherin-11 depletion on proliferation of cells.
Figure 17C:
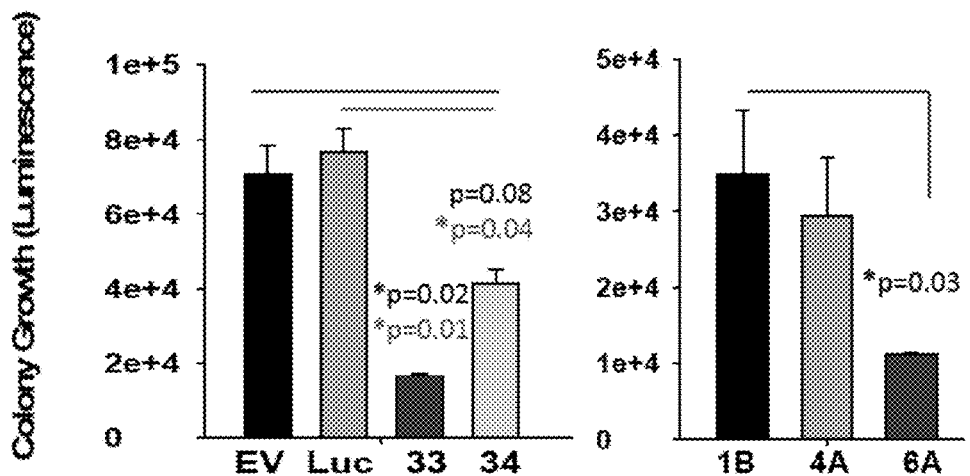
FIG. 17C shows graphs of the effect of cadherin-11 depletion on anchorage-independent colony growth of cells.

Cell adhesion affects cellular proliferation throughout development and in tumorigenesis, and depletion of endogenous cadherin-11 in smooth muscle cells significantly inhibits their proliferation. Cadherin-11 knockdown significantly decreased proliferation in MDA-MB-231 and PC-3 cancer cells (FIGS. 11B, 17B, and 17C). Anchorage-independent growth of basal-B type MDA-MB-231 breast and PC-3 prostate cancer cells was also significantly reduced following cadherin-11 knockdown (FIG. 11C).

Figure 12A:
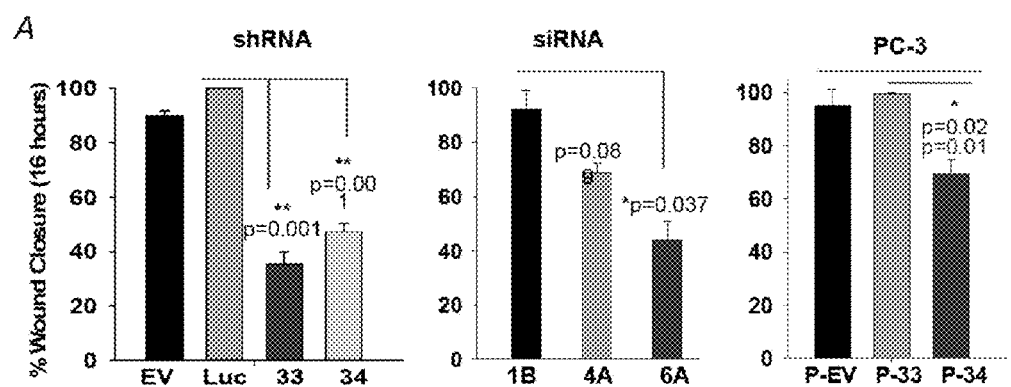
FIG. 12A shows bar graphs demonstrating that cadherin-11 depletion significantly reduces the migration of stable cells into wounds as measured by time-lapse imaging from three separate fields (triplicate wells, 24-well plate) 16 hours after wounding. Columns and bars show the mean and SEM, respectively.
Figure 12B:
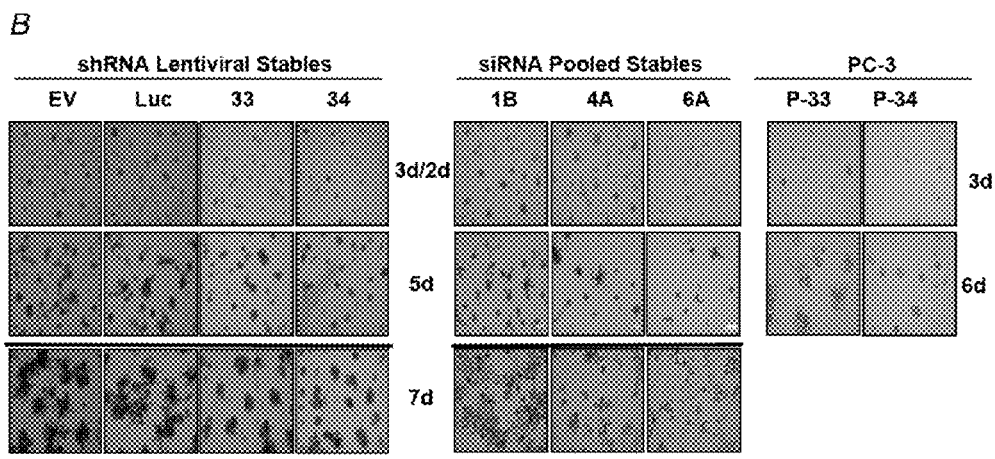
FIG. 12B shows pictures that show cadherin-11 depletion delays formation of branched networks on Matrigel.

Cadherin-11 Alters Migratory and Invasive Potential of Breast and Prostate Cancer Cells. Reduction of cadherin-11 in MDA-MB-231 breast and PC-3 prostate cancer cells significantly decreased their migration in wound healing assays (FIG. 12A). The phenotype of cadherin-11 knockdown cells in a 3-dimensional matrix was next examined. MDA-MB-231 breast and PC-3 prostate cancer cells cultured on Matrigel basement membrane-like matrix form branched networks within one week. It was observed that control cells containing either empty vector or scrambled target sequence also form networks throughout Matrigel within 7 days (FIG. 12B). Cadherin-11 depleted cells failed to form networks their first week in culture, however, over the ensuing week, the cells formed networks that were indistinguishable from controls. Prostate cancer cells displayed a similar delayed network formation phenomenon (FIG. 12B).

Figure 13A:
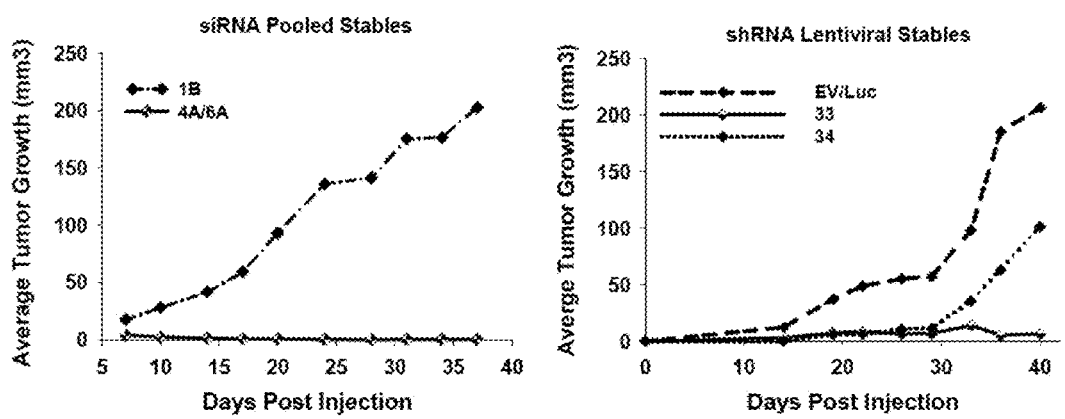
FIG. 13A shows graphs displaying the tumor volume in athymic nude mice injected s.c. with MDA-MB-231 cells stably expressing cadherin-11 siRNA or shRNA. The tumor volume was measured 2× per week for at least 40 days.
Figure 13B:
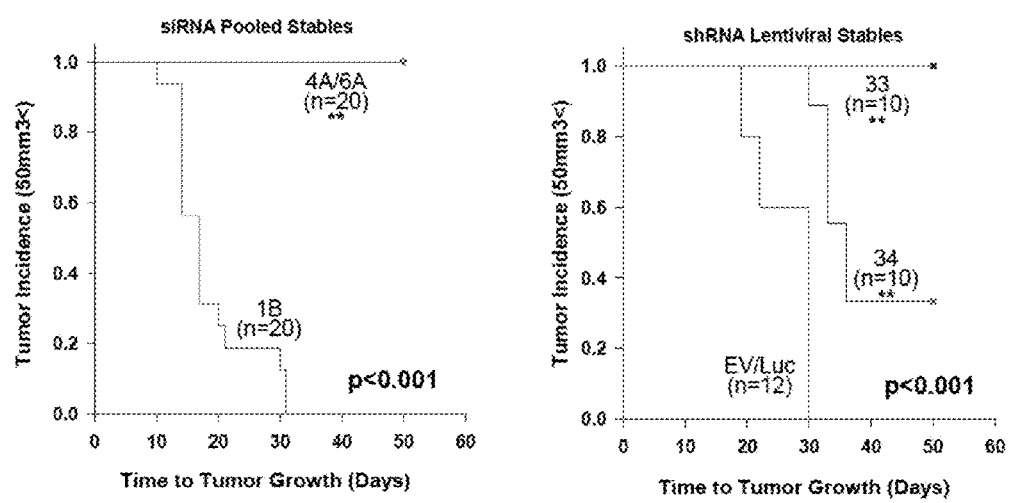
FIG. 13B shows Kaplan-Meier analysis log-rank test (p<0.001) of tumor incidence/latency of MDA-MB-231 cells in nude mice.

Cadherin-11 is Required for Subcutaneous Tumor Growth In Vivo. MDA-MB-231 cells readily form tumors in nude mice. Stable control or knockdown cells were subcutaneously injected into athymic nude mice and tumor growth assessed twice weekly with calipers for 6 weeks. Cells containing siRNA targeting cadherin-11 completely failed to form tumors in nude mice, whereas the empty vector controls formed subcutaneous tumors (FIG. 13). This experiment was repeated several times and none of the 26 cadherin-11 knockdown cell injections resulted in a significant tumor. Likewise, stable cell lines containing shRNA-targeted sequences displayed significant delay to onset of tumor growth compared to empty vector or scrambled sequence controls. However, after about one month, subcutaneous tumors began to form from injections of one lentivirally-infected shRNA stable cell (FIG. 13). Once palpable, these tumors progressed at a similar rate to empty vector and scrambled controls. However, in vitro Western blot results indicate these cells began to re-express cadherin-11 at that time, and in the absence of selection media. These data, along with functional assays in vitro, show that cadherin-11 is necessary for tumor growth in MDA-MB-231 breast cancer cells. They further show that cadherin-11 provides a viable therapeutic target in epithelial cancers with increased cadherin-11 expression.

Cadherin-11 Knockdown Alters the Expression of Genes Associated with Poor Prognosis Malignancies. Microarray analysis was performed using Affymetrix U133-A arrays to determine genes significantly altered upon depletion of cadherin-11 in aggressive breast cancer cells (see Materials and Methods). Empty vector controls (RNAi 1B) were compared with two different stable knockdown cell lines (RNAi 4A and 6A) on three separate occasions. An inter-sample comparison was performed separately among the controls and then the four cadherin-11 (CDH11) depleted samples, and outlying genes differing greater than 1.5 fold among respective groups were excluded from further analyses (FIG. 14A). Resulting control and knockdown gene sets were compared to one another using a significance minimum of $p<0.01$, yielding 187 differentially expressed genes comprising gene ontology classes including cell adhesion, signaling and movement, cancer, connective tissue and inflammatory diseases (FIG. 14B). Many of these genes were associated with poor prognosis cancers and the stromal cell signature predictive of poor outcome in breast cancer patients. Twenty-four genes were common to the Wang dataset examining breast cancer relapse (FIG. 14C). Multiple cellular adhesion genes (COL5A1, ITGB3, and THBS1) are affected by cadherin-11 depletion in breast cancer, along with reduction of known EMT markers (SMAD6 and SNAI2) and metalloproteinase family genes (ADAM and TIMP3) associated with aggressive cancers and metastasis. Additionally, cadherin-11 reduction significantly increases putative tumor suppressor genes NOL7 and PRSS3. Together these data indicate that cadherin-11 regulates expression of genes important in basal-B breast cancer cells, along with poor prognosis malignancies of the breast, prostate, brain, plasma cell, and kidney.

Figure 1B:
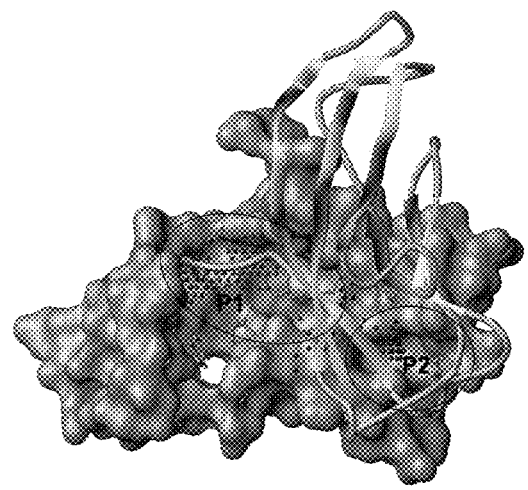
FIG. 1B is a schematic showing the EC1 homodimer interface of cadherin-11.
Figure 15A:
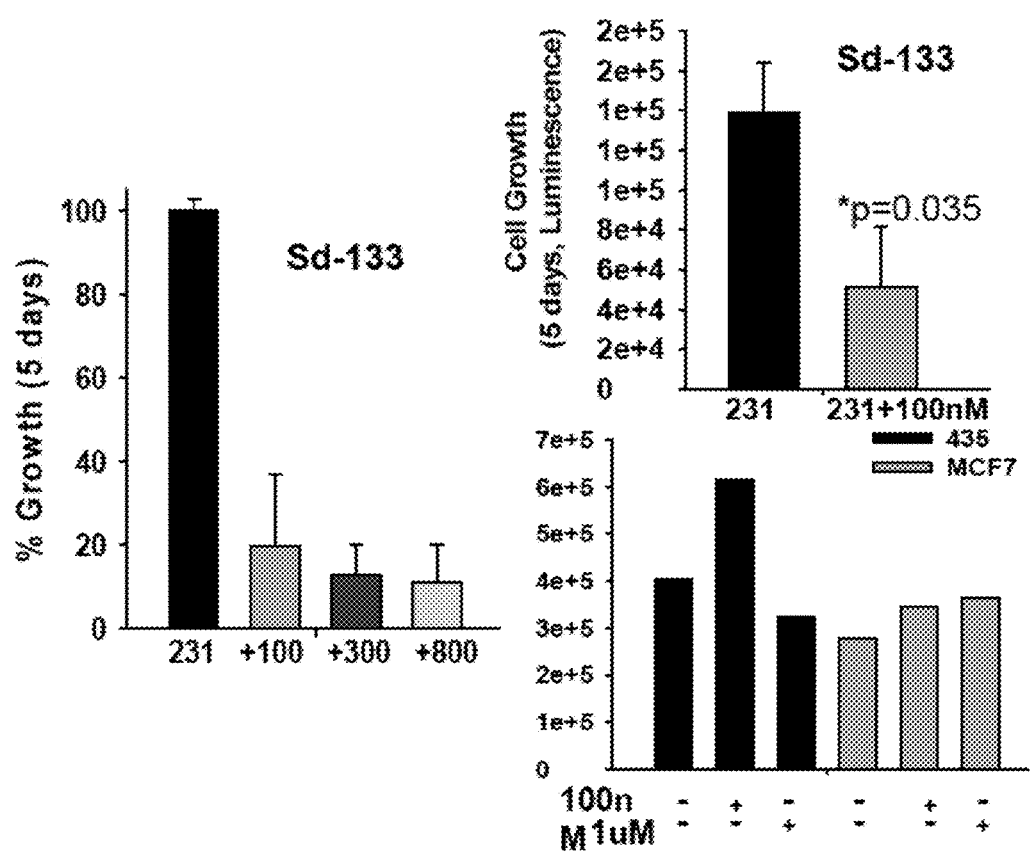
FIG. 15A is a graph showing the cell growth of MDA-MB-231, caherin-11 (CDH11)-negative MDA-MB-435 melanoma, and MCF7 breast cancer cell lines after treatment with Compound 1.
Figure 15B:
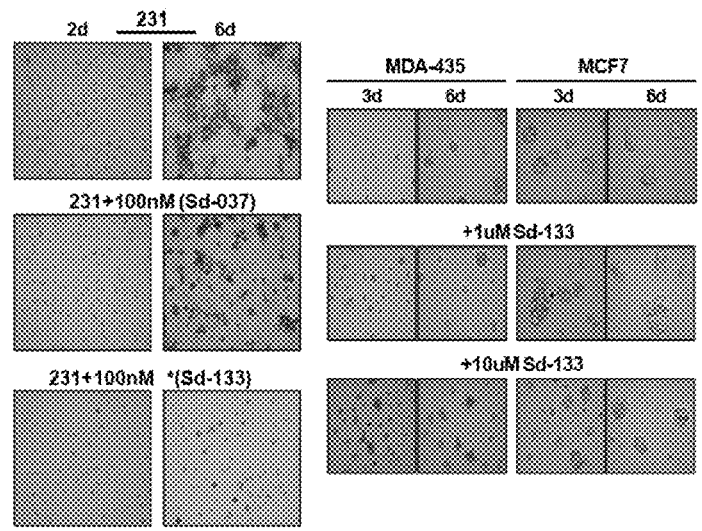
FIG. 15B, left panel, shows pictures of MDA-MB-231 cells untreated (231), treated with Compound 9 (231+100 nM (Sd-037)), and treated with Compound 1 (231+100 nM (Sd-133)) after two and six days. The right panel shows pictures of MDA-MB-435 and MCF7 cells untreated (MDA-435 and MCF7), treated with 1 Compound 1 (+1 µM Sd-133), and treated with 10 µM Compound 1 (+10 µM Sd-133) after three and six days FIG. 15C, left panel, shows a bar graph showing the cell growth of untreated MDA-MB-231 cells (231) and cells treated with 100 nM of Compound 1 (231+100 nM Sd-133) and the corresponding pictures of the cells. The middle panel is a bar graph showing the colony number and size of the colony for untreated cells (231+DMSO) and cells treated with 100 nM of Compound 1 (231+Sd-133(100 nM)). The right panel shows a bar graph showing the cell growth of untreated MDA-435 or MCF7 cells and cells treated with 100 nM of Compound 1 (+100 nM Sd-133) and the corresponding pictures of the cells.
Figure 15C:
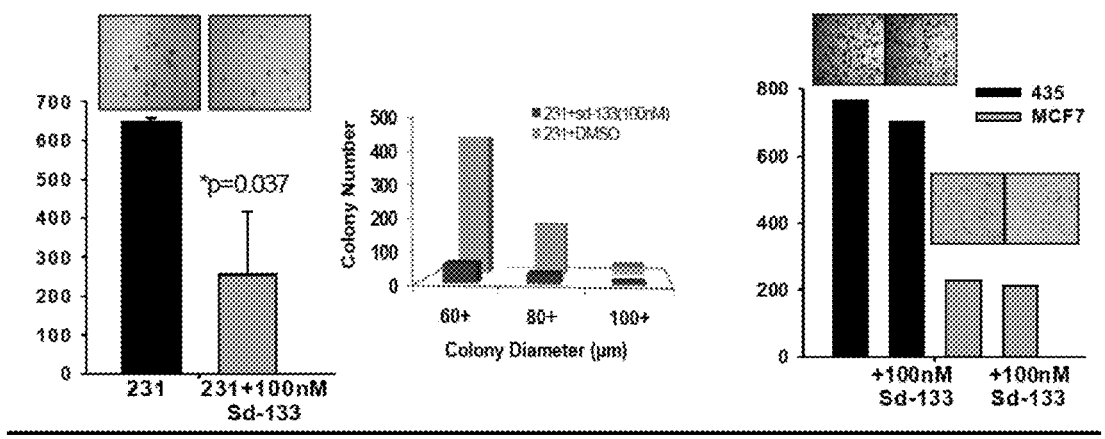

Small Molecule Cadherin-11 Inhibitors Specifically Inhibit Cadherin-11 Function In Vitro. Cadherin-11 association with certain poor prognosis cancers, proliferation of basal-type breast cancer cells, and tumorigenesis in mice make it a viable therapeutic target for these malignancies. The crystal structure of cadherin-11 reveals unique binding pockets as potential sites for interference of cell-cell adhesion (FIG. 1B). A computer-based method of structural modeling was used to predict conformations capable of binding these specific hydrophobic pockets. The ectodomain1 (EC1) dimer adhesive interface is formed by exchange of N-terminal β strands between two cadherin-11 molecules. The dimer interface has a large hydrophobic region (unique to type II cadherins) with two conserved tryptophan residues. It was reasoned that a small molecule blocking cadherin-11 EC1 dimer formation would potentially inhibit cadherin-11 function. This structure was used to base molecular simulations and produce pharmacophores designed to block one or both of the two adjacent regions (P1 and P2) predicted necessary for cadherin-11 function in cell-cell adhesion. Three in-silico strategies were implemented: 1) generation of flexible receptor conformations, 2) receptor-based dynamic pharmacophore screening and 3) small molecule docking simulations. The 29 most promising candidates identified by in silico screen were subjected to free energy simulations at 100 picosecond intervals, taking into consideration the induced fit effect, which accounts for conformation flexibility both before and after binding/docking simulations. All critical interactions between tryptophan and the cadherin-11 EC1 domain were included, except E87 and D27 which showed high flexibility upon solvent exposure. These 29 compounds were purchased commercially and tested. Many of the compounds initially screened inhibited cadherin-11 function at 10 µM range, attesting to the in silico screening efficiency. Three compounds, Compound 1 (Sd-133), Compound 9 (Sd-037), and Compound 10 (Sd-073), were effective in nanomolar ranges. Compound 1 significantly inhibited MDA-MB-231 cell proliferation, colony growth, and invasion at 100 nM (FIG. 15A-C). The inhibitor failed to alter proliferation or invasion in MDA-MB-435 melanoma cells (expressing N-cadherin) and MCF7 breast cancer cells (expressing E and P-cadherin) at 1 µM and 10 µM concentrations, indicating specificity for cadherin-11-expressing cells (FIG. 15A-C). The potency of Compound 1 likely stems from its shape and moderate structural flexibility, enabling it to accommodate to and bind tightly within the tryptophan binding pocket. Though this pocket is largely hydrophobic, a network of hydrogen bonds between Compound 1 and R23, H25, P88, S90 confers specificity and rigid binding. Hydrophobic interaction of Compound 1 with F7, L24, S26, Y37, A75, A77, E87, S90, and F92 may also contribute to its action. Furthermore, the mobility of the water molecule located near S90 allows possible adjustment of its position to form hydrogen bonds with the inhibitors. Two other potent inhibitors, Compound 9 and 10, have similar interactions with the tryptophan pocket. The water mediated H-bond is observed with all three inhibitors after 500 picosecond MD simulations run to include induced fit effects. All three inhibitors compete for tryptophan binding and interact with the same residues including the water molecule formed by the two tryptophans. Superimposition of Compounds 1, 9, and 10 within the tryptophan pocket clearly shows the hydrophobic moieties of these inhibitors occupy the same space as that of hydrophobic tryptophans. Collectively, these data show cadherin-11 is important for tumor progression in cancers, including poor prognostic cancers, expressing it.

Example 13

Cell Aggregation Assay

Figure 16A:
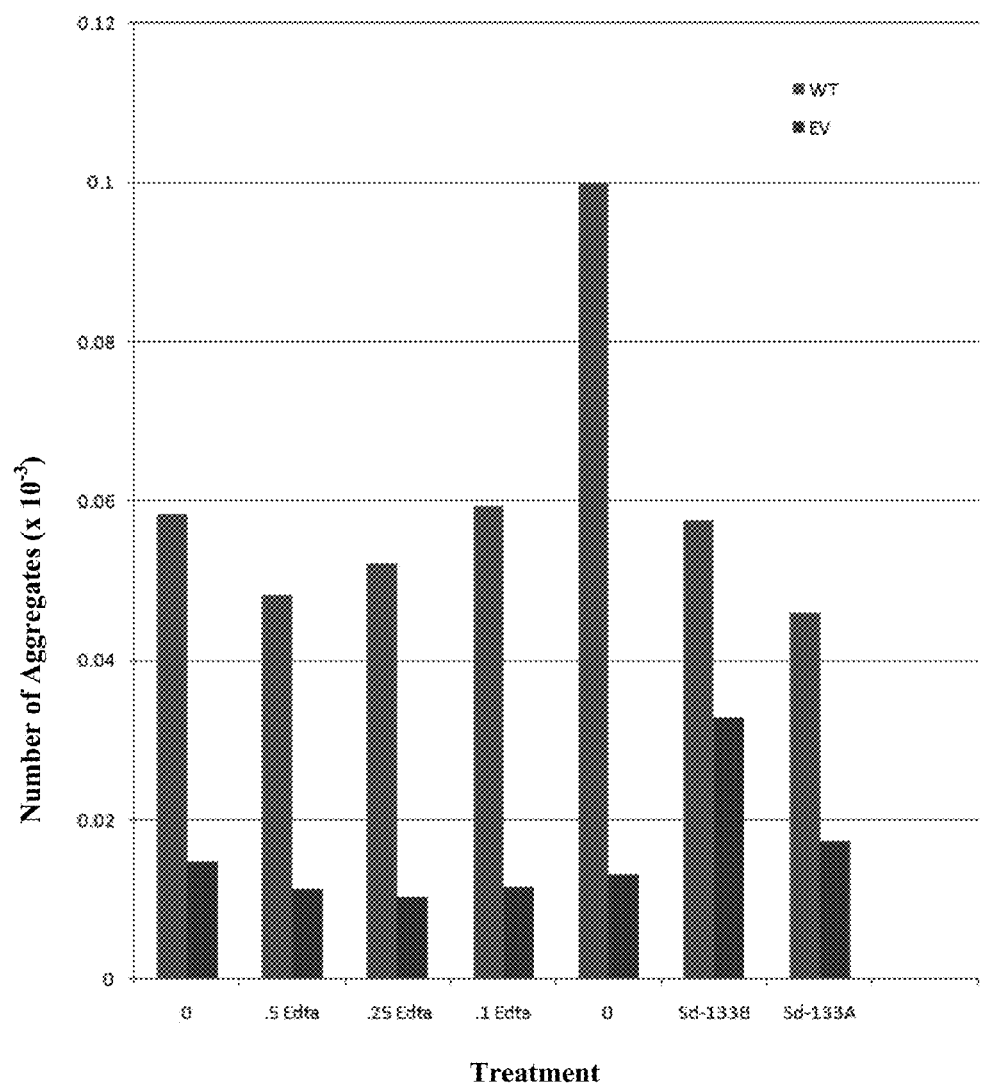
FIGS. 16A and B are graphs showing the cell aggregation for cells with empty vectors or cells with stably-transfected cadherin-11. The cells were either untreated, treated with EDTA (0.5 mM, 0.25 mM, or 0.1 mM), treated with 1 µM of Compound 1 (Sd-133), treated with 1 µM of Compound 2 (Sd-133A), treated with 1 µM of Compound 3 (Sd-133B), treated with 1 TM of Compound 11 (Sd-12), treated with 1 TM of Compound 12 (Sd-48), treated with 1 TM of Compound 17 (Sd-20), treated with 1 TM of Compound 18 (Sd-51), treated with 1 TM of Compound 19 (Sd-22), or treated with 1 TM of Compound 20 (Sd-23).
Figure 16B:
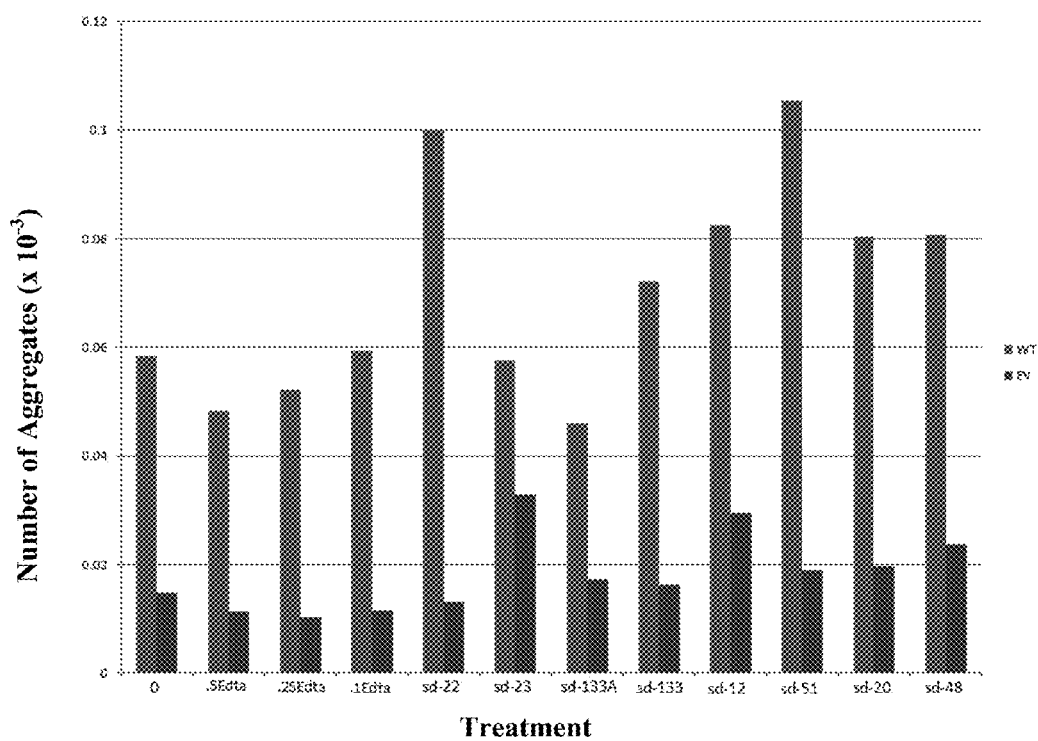

Cell aggregation assays were performed on L-cells with stably-transfected empty vector or cadherin-11. The cells were seeded and grown overnight, trypsinized with additional EDTA, resuspended in DMEM with 20% FBS, and counted. The cells were spun down and resuspended in DMEM containing no treatment, 0.5 mM EDTA, 0.25 mM EDTA, 0.1 mM EDTA, or cadherin-11 inhibitors including 1 TM of Compound 1 (Sd-133), 1 TM of Compound 2 (Sd-133A), 1 TM of Compound 3 (Sd-133B), 1 TM of Compound 11 (Sd-12), 1 TM of Compound 12 (Sd-48), 1 TM of Compound 17 (Sd-20), 1 TM of Compound 18 (Sd-51), 1 TM of Compound 19 (Sd-22), or 1 TM of Compound 20 (Sd-23). The cells were allowed to recover for one hour and were then put into uncoated 12 well plates and shaken for one hour at 100 rpm at 2.25×105 cells/mL. The cells were then counted using Microsizer Coulter Counter (Beckman Coulter, Inc; Brea, Calif.). Counts over 20 uM in length were considered aggregates, while counts below 20 uM were considered as single cells. The counts were confirmed by manual counting. As shown in FIGS. 16A and 16B, under these conditions, the cadherin-11 cells treated with at least Compounds 2 and 3 showed a decrease in aggregate formation, while the empty vector transfected cells remained stable.

Example 14

In Vivo Toxicity Data

Female Balb/c mice, 8-12 weeks old, were obtained from the National Cancer Institute (Bethesda, Md.). A stock solution of 200 mg/ml of Compound 1 was prepared with a 1:1 ratio of DMSO and PEG. The working solution was diluted with PEG. Compound 1 (Sd-133) was administered at a constant volume (0.01 ml/1 g body weight) over the range of doses to be tested by varying the concentration of the dosing preparation according to the OECD Acute Toxicity-Up-and Down Procedure. A test dose was administered to one animal by IP injection and the animal was observed for 14 days. Observations included toxicity onset time, symptoms, duration and the time elapsed for recovery or death. Based on the study, the LD50 of Compound 1 was estimated at 2000 mg/kg.

Example 15

Cadherin-11 is Required for the Growth and Invasion of Glioblastoma Cell Line LN229

Figure 18A:
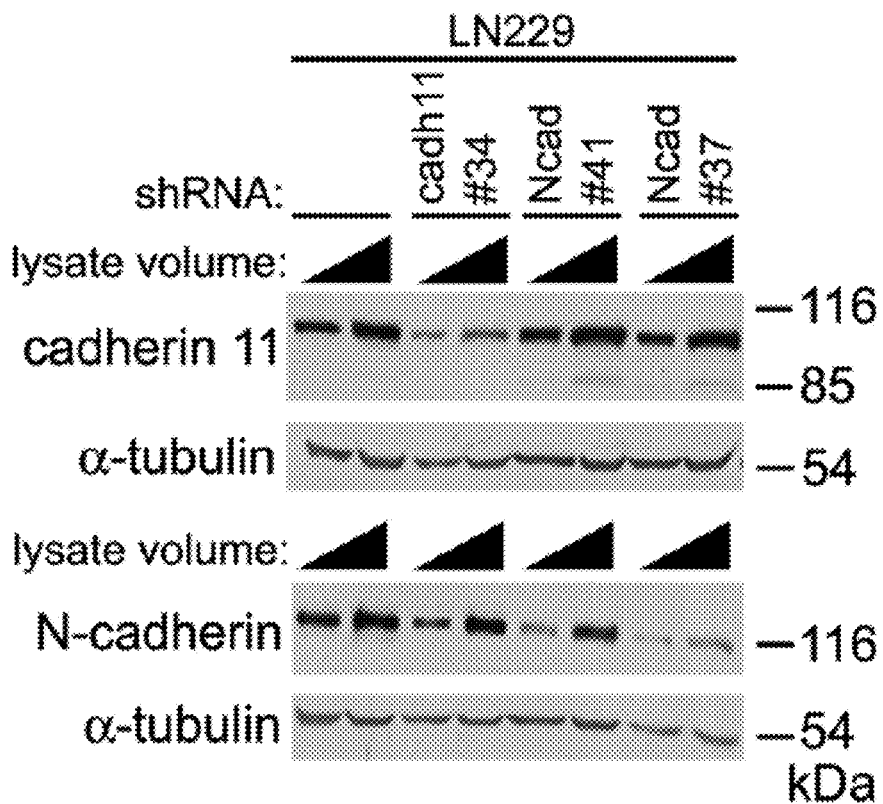
FIG. 18A shows images of the inhibition of cadherin-11 and N-cadherin expression with lentivirus containing shRNA in glioblastoma cell line LN229.
Figure 18B:
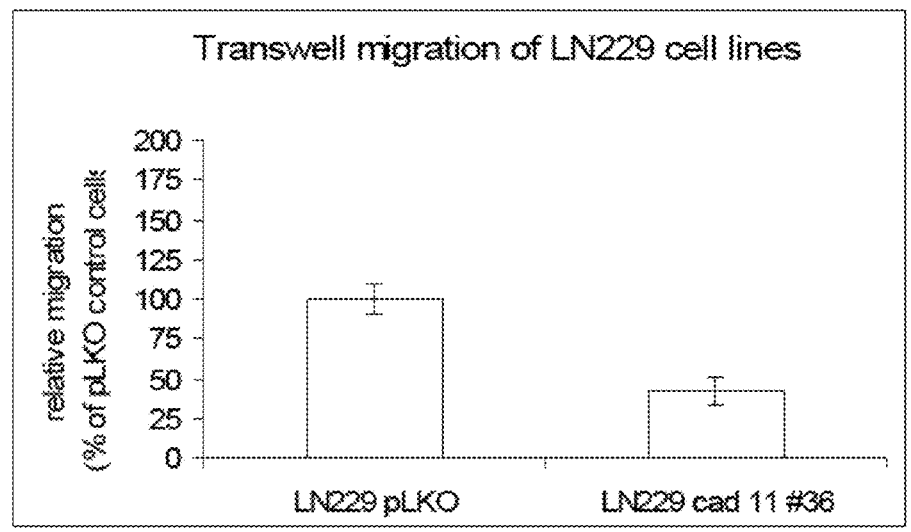
FIG. 18B is a graph showing the relative migration of control LN229 cell lines (LN229 pLKO) and cell lines with inhibited expression of cadherin-11 (LN229 cad 11 #36).
Figure 18C:
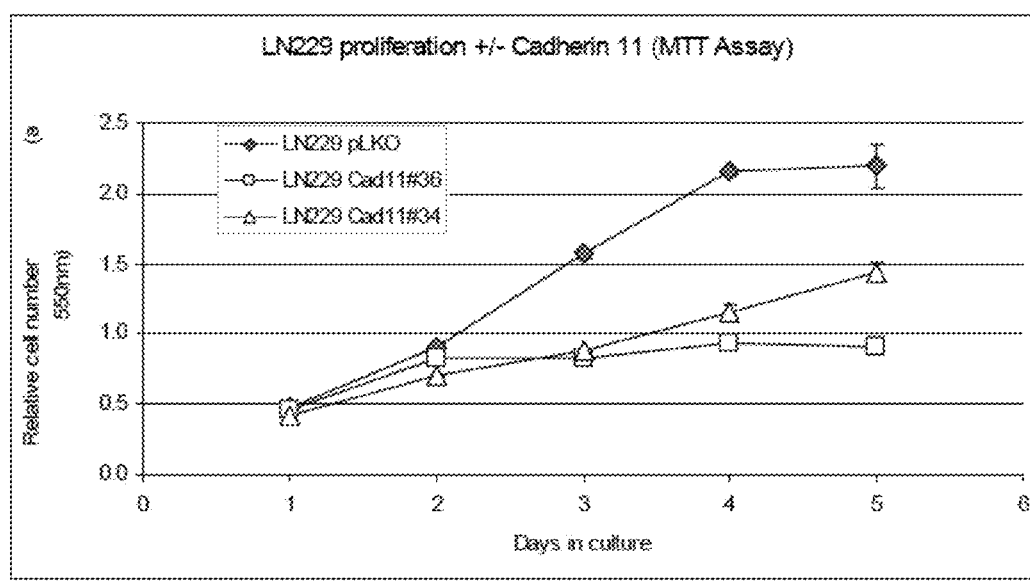
FIG. 18C is a graph showing the cell proliferation of control LN229 cell lines (LN229 pLKO) and cell lines with inhibited expression of cadherin-11 (LN229 Cad11#36 and LN229 Cad11#34).

Cadherin-11 or N-cadherin was knocked down in LN229 cells using shRNA according to methods described in Example 12. A significant reduction in cadherin-11 and N-cadherin protein 48 hours after infection with lentivirus containing shRNA was shown (FIG. 18A). Knockdown of cadherin-11 reduces in vitro invasion (FIG. 18B) and growth of LN229 cells (FIG. 18C). These data show that cadherin-11 expression in glioblastoma cells is required for their continued growth and invasion in vitro. In the three tumor types in which cadherin-11 is associated with poor prognosis, including basal-like breast and prostate cancers and glioblastoma, its expression is important for their growth and invasion.

Example 16

In Vivo Antibody Treatment

Mice bearing MDA-231, LN229, or PC3 xenografted tumors will be injected IP with 50 μg/kg of a cadherin-11 antibody or control IgG at weekly intervals for 60 days. Tumor growth will be monitored and the effects of the cadherin-11 antibody will be compared to animals bearing MDA435 cell xenografts expressing N-cadherin.

What is claimed is:

1. A compound of the following formula:

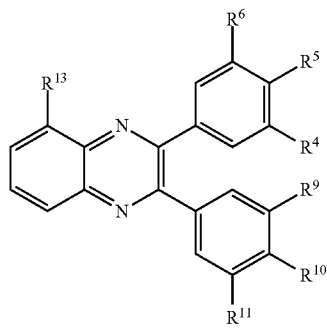

or a pharmaceutically acceptable salt thereof, wherein:
$R^4$, $R^5$, $R^6$, $R^9$, $R^{10}$, and $R^{11}$ are each independently selected from hydrogen, halogen, hydroxyl, substituted or unsubstituted alkoxy, substituted or unsubstituted amido, substituted or unsubstituted amino, substituted carbonyl, substituted or unsubstituted alkyl, unsubstituted or unsubstituted alkenyl, substituted or unsubstituted alkynyl, unsubstituted heteroalkyl, unsubstituted or unsubstituted heteroalkenyl, substituted or unsubstituted heteroalkynyl, substituted or unsubstituted cycloalkyl, unsubstituted or unsubstituted cycloalkenyl, substituted or unsubstituted cycloalkynyl, substituted or unsubstituted heterocycloalkyl, unsubstituted or unsubstituted heterocycloalkenyl, substituted or unsubstituted heterocycloalkynyl, substituted or unsubstituted aryl, and substituted or unsubstituted heteroaryl; and
$R^{13}$ is halogen, hydroxyl, substituted or unsubstituted alkoxy, substituted or unsubstituted amido, substituted or unsubstituted amino, substituted or unsubstituted alkyl, unsubstituted or unsubstituted alkenyl, substituted or unsubstituted alkynyl, unsubstituted heteroalkyl, unsubstituted or unsubstituted heteroalkenyl, substituted or unsubstituted heteroalkynyl, substituted or unsubstituted cycloalkyl, unsubstituted or unsubstituted cycloalkenyl, substituted or unsubstituted cycloalkynyl, substituted or unsubstituted heterocycloalkyl, unsubstituted or unsubstituted heterocycloalkenyl, substituted or unsubstituted heterocycloalkynyl, substituted or unsubstituted aryl, or substituted or unsubstituted heteroaryl, wherein at least one of $R^5$ and $R^{10}$ is hydroxyl.

2. The compound of claim 1, wherein $R^5$ is hydroxyl.

3. The compound of claim 1, wherein $R^6$ is chloro.

4. The compound of claim 1, wherein $R^{10}$ is hydroxyl.

5. The compound of claim 1, wherein $R^{13}$ is hydroxyl or chloro.

6. The compound of claim 1, wherein the compound is:

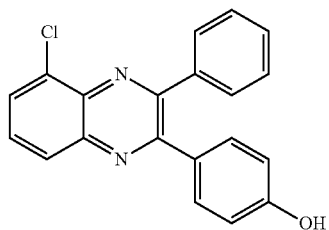

or a pharmaceutically acceptable salt thereof.

7. The compound of claim 1, wherein the compound is:

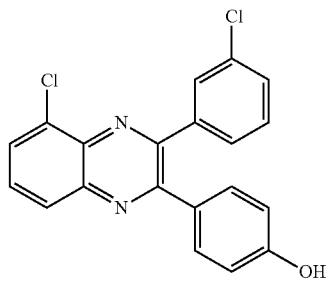 [SMILES: Oc1ccc(-c2nc3cccc(Cl)c3nc2-c2cccc(Cl)c2)cc1]

or a pharmaceutically acceptable salt thereof.

8. The compound of claim 1, wherein the compound is:

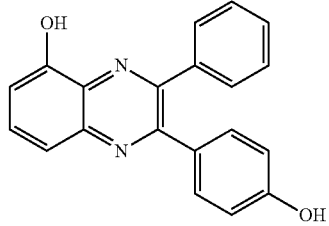 [SMILES: Oc1ccc(-c2nc3cccc(O)c3nc2-c2ccccc2)cc1]

or a pharmaceutically acceptable salt thereof.

9. The compound of claim 1, wherein the compound is:
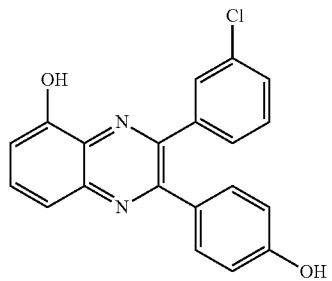
or a pharmaceutically acceptable salt thereof.
10. A pharmaceutical composition comprising a compound of claim 1 and a pharmaceutically acceptable carrier.
11. A compound of the following formula:
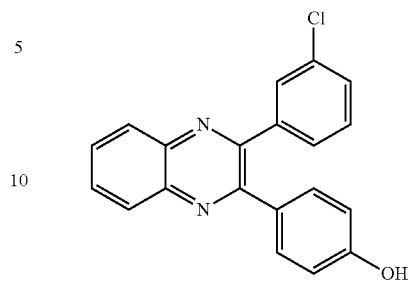
or a pharmaceutically acceptable salt thereof.
* * * * *

UNITED STATES PATENT AND TRADEMARK OFFICE
CERTIFICATE OF CORRECTION

PATENT NO. : 9,889,131 B2
APPLICATION NO. : 15/017040
DATED : February 13, 2018
INVENTOR(S) : Stephen W. Byers et al.

Page 1 of 1

It is certified that error appears in the above-identified patent and that said Letters Patent is hereby corrected as shown below:

In the Claims

Column 43, Lines 47-48, in Claim 1, delete "unsubstituted or unsubstituted alkenyl" and insert --substituted or unsubstituted alkenyl--

Column 43, Lines 49-50, in Claim 1, delete "unsubstituted or unsubstituted heteroalkenyl" and insert --substituted or unsubstituted heteroalkenyl--

Column 43, Lines 53-54, in Claim 1, delete "unsubstituted or unsubstituted cycloalkenyl" and insert --substituted or unsubstituted cycloalkenyl--

Column 43, Lines 55-56, in Claim 1, delete "unsubstituted or unsubstituted heterocycloalkenyl" and insert --substituted or unsubstituted heterocycloalkenyl--

Column 43, Line 65, in Claim 1, delete "unsubstituted or unsubstituted alkenyl" and insert --substituted or unsubstituted alkenyl--

Column 43, Line 67, in Claim 1, delete "unsubstituted or unsubstituted heteroalkenyl" and insert --substituted or unsubstituted heteroalkenyl--

Column 44, Lines 2-3, in Claim 1, delete "unsubstituted or unsubstituted cycloalkenyl" and insert --substituted or unsubstituted cycloalkenyl--

Column 44, Lines 6-7, in Claim 1, delete "unsubstituted or unsubstituted heterocycloalkenyl" and insert --substituted or unsubstituted heterocycloalkenyl--

Signed and Sealed this
Thirty-first Day of July, 2018

Andrei Iancu
*Director of the United States Patent and Trademark Office*

UNITED STATES PATENT AND TRADEMARK OFFICE
CERTIFICATE OF CORRECTION

PATENT NO. : 9,889,131 B2
APPLICATION NO. : 15/017040
DATED : February 13, 2018
INVENTOR(S) : Stephen W. Byers et al.

Page 1 of 1

It is certified that error appears in the above-identified patent and that said Letters Patent is hereby corrected as shown below:

In the Specification

In Column 1, Lines 18-24, delete:
"STATEMENT REGARDING FEDERALLY FUNDED RESEARCH
This invention was made with government support under Grant No. DOD BC062416-01 awarded by the Department of Defense. The government has certain rights in the invention."

And insert:
-- STATEMENT REGARDING FEDERALLY FUNDED RESEARCH
This invention was made with government support under Grant numbers W81XWH-07-1-0609 and W81XWH-08-1-0545 awarded by the Department of Defense. The government has certain rights in the invention. --.

Signed and Sealed this
Ninth Day of January, 2024

Katherine Kelly Vidal
*Director of the United States Patent and Trademark Office*